US012758398B2

(12) United States Patent
Essayan et al.

(10) Patent No.: US 12,758,398 B2
(45) Date of Patent: Oct. 13, 2026

(54) INSERTER FOR SPINAL FUSION IMPLANT

(71) Applicant: NuVasive, Inc., San Diego, CA (US)

(72) Inventors: Gregory Essayan, San Diego, CA (US); Alex Pham, San Diego, CA (US); Stephen Laffoon, San Diego, CA (US); Wei-Hsiang Chang, San Diego, CA (US); Elizabeth Perry, San Diego, CA (US); Alejandro De La Rosa, San Diego, CA (US); Mary Hayles, San Diego, CA (US)

(73) Assignees: NuVasive, Inc., San Diego, CA (US); Globus Medical Inc., Audubon, PA (US)

( * ) Notice: Subject to any disclaimer, the term of this patent is extended or adjusted under 35 U.S.C. 154(b) by 290 days.

(21) Appl. No.: 18/560,863

(22) PCT Filed: May 11, 2022

(86) PCT No.: PCT/US2022/028802

§ 371 (c)(1),
(2) Date: Nov. 14, 2023

(87) PCT Pub. No.: WO2022/241011

PCT Pub. Date: Nov. 17, 2022

(65) Prior Publication Data

US 2024/0285416 A1 Aug. 29, 2024

Related U.S. Application Data

(60) Provisional application No. 63/188,763, filed on May 14, 2021.

(51) Int. Cl.
*A61F 2/46* (2006.01)

(52) U.S. Cl.
CPC ..... *A61F 2/4611* (2013.01); *A61F 2002/4627* (2013.01)

(58) Field of Classification Search
CPC ............ A61F 2/4611; A61F 2002/4627; A61F 2002/4615; A61F 2002/4629
See application file for complete search history.

(56) References Cited

U.S. PATENT DOCUMENTS

| | | | | |
|---|---|---|---|---|
| 8,187,334 | B2 * | 5/2012 | Curran | A61F 2/4611 623/17.16 |
| 8,673,005 | B1 * | 3/2014 | Pimenta | A61F 2/447 623/17.11 |
| 10,478,313 | B1 * | 11/2019 | Sweeney, III | A61F 2/4611 |
| 12,533,164 | B2 * | 1/2026 | Lopez Camacho | A61B 17/72 |
| 12,539,145 | B2 * | 2/2026 | Bae | A61B 17/7016 |
| 12,539,148 | B2 * | 2/2026 | Goel | A61B 17/7056 |
| 2014/0277493 | A1 | 9/2014 | Glad et al. | |
| 2017/0105844 | A1 | 4/2017 | Kuyler et al. | |
| 2017/0189204 | A1 | 7/2017 | Riemhofer et al. | |

* cited by examiner

*Primary Examiner* — Ellen C Hammond

(57) ABSTRACT

Disclosed herein are dismantlable inserters for use in spinal fusion implant procedures, methods for engaging an implant using such inserters, methods of disengaging an implant from such inserters, and methods for disassembling such inserters, as well as systems including such inserters and corresponding implants.

13 Claims, 31 Drawing Sheets

FIG. 2B
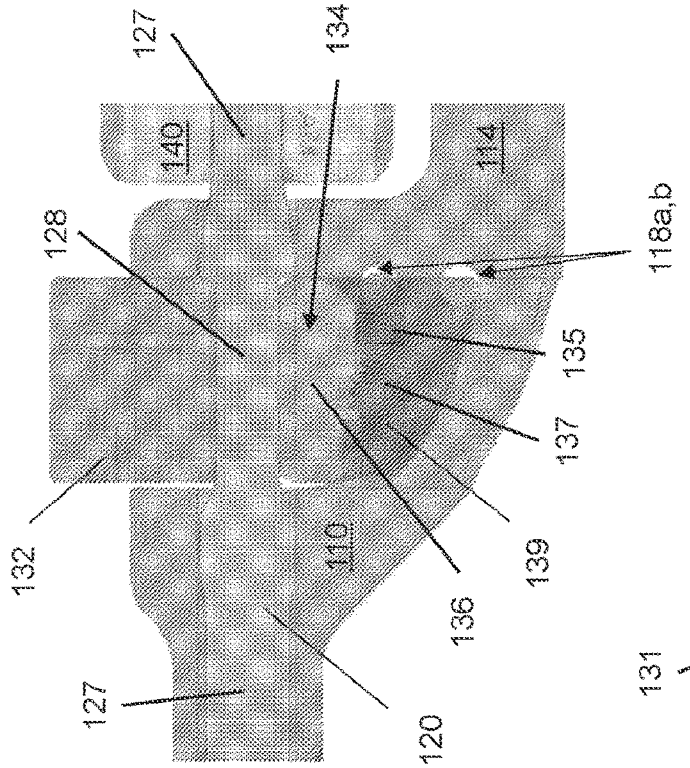
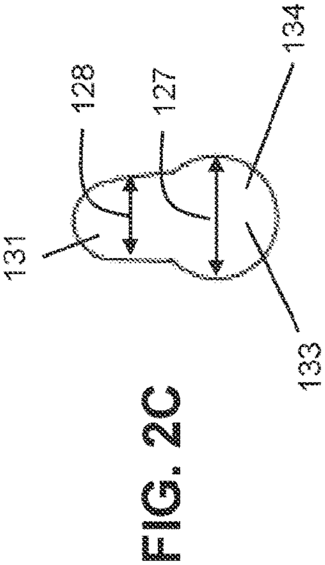
FIG. 2C
FIG. 2A
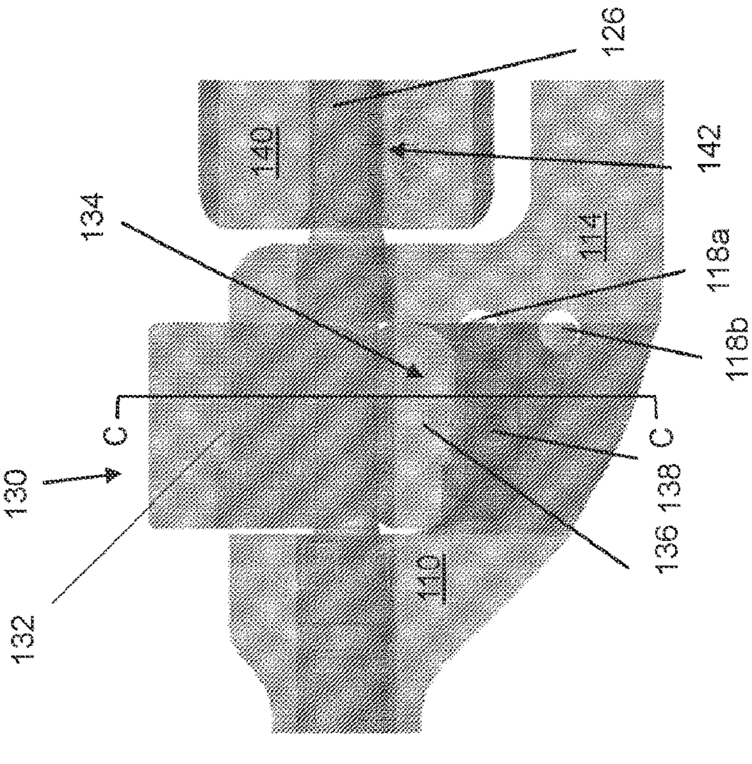

INSERTER FOR SPINAL FUSION IMPLANT

CROSS REFERENCE TO RELATED APPLICATION

The present patent application claims priority to U.S. Provisional Patent Application No. 63/188,763, filed on May 14, 2021, which is incorporated by reference as though fully set forth herein.

BACKGROUND

Back problems are a common and debilitating medical occurrence, resulting in over 500,000 spinal lumbar and cervical fusion procedures performed each year in the United States alone. One of the causes of back pain and disability results from the rupture or degeneration of one or more intervertebral discs in the spine.

Surgical procedures are commonly performed to correct problems with displaced, damaged, or degenerated intervertebral discs due to trauma, disease, or aging. Generally, spinal fusion procedures involve removing some or all of the diseased or damaged disc, and inserting one or more intervertebral implants into the resulting disc space.

It is desirable to provide improved instruments for use during spinal surgical procedures, including instruments used to insert spinal fusion implants.

SUMMARY

A first aspect of the disclosure provides an inserter for inserting a spinal fusion implant, the inserter comprising: a housing having a proximal member and a housing shaft extending distally therefrom; an inner shaft having a distal end and a proximal end, wherein the inner shaft is configured to be disposed at least partially within the housing shaft, and to translate relative to the housing shaft. The distal end of the inner shaft is configured to releasably engage the spinal fusion implant. A thumbwheel is configured to be rotatably fixed to the proximal end of the inner shaft, and to rotate about a longitudinal axis of the inserter, thereby causing the inner shaft to rotate. A lock is engaged with the inner shaft, wherein the lock is configured to move between a locked position and an unlocked position. In the locked position, the inner shaft is rotatably fixed to the thumbwheel, while in the unlocked position, the inner shaft and the thumbwheel are separable from one another. A soft stop is configured to provide one or more of audible and or tactile feedback to a user to indicate that the spinal fusion implant is fully disengaged from the distal end of the inner shaft.

In certain embodiments, the distal end of the inner shaft comprises threads configured to engage complementary threads on the spinal fusion implant.

In certain embodiments, rotation of the thumbwheel in a first direction is configured to cause the distal end of the inner shaft to engage the spinal fusion implant, and rotation of the thumbwheel in a second direction is configured to cause the distal end of the inner shaft to disengage from the spinal fusion implant.

In certain embodiments, in the unlocked position, the inner shaft is configured to translate distally, causing the proximal end thereof to disengage from the thumbwheel. The inner shaft is further configured to be removed from a distal end of the housing shaft in order to dismantle the inserter.

In certain embodiments, the thumbwheel further comprises a biasing element configured to bias the thumbwheel in a distal direction. In the unlocked position, the thumbwheel is configured to translate proximally against a force of the biasing element. When the proximal end of the inner shaft is disengaged from the thumbwheel, a distal end of the thumbwheel is configured to move radially outward relative to the longitudinal axis to initiate disassembly of the thumbwheel from the inserter.

In certain embodiments, the proximal end of the inner shaft comprises a keyed feature which provides a complementary fit with a corresponding keyed feature on the thumbwheel.

In certain embodiments, the keyed feature is a male hex feature, and the corresponding keyed feature is a female hex feature.

In certain embodiments, the inner shaft has a first diameter, and the lock further comprises: a portion of the inner shaft having a second diameter that is reduced relative to the first diameter; and a lock button disposed on the housing and movable in a direction substantially perpendicular to the longitudinal axis. The lock button comprises a slot configured to engage the portion of the inner shaft having the reduced diameter. The slot has an irregular cross sectional shape, such that in the locked position, an outer surface of the lock button is substantially flush with an outer surface of the housing, and a first end of the slot provides a close fit with the portion of the inner shaft having the reduced diameter. In the unlocked position, the outer surface of the lock button is raised relative to the outer surface of the housing, and a second end of the slot accommodates the inner shaft at a portion not having the reduced diameter, allowing the inner shaft to translate.

In certain embodiments, the lock further comprises a track extending within the lock button in a direction parallel to the direction in which the lock button is movable; a pin disposed within the track; a plunger disposed within the housing and configured to engage the lock button in the locked position and the unlocked position; a spring configured to engage the plunger; and a screw configured to maintain a position of the plunger and the spring.

In certain embodiments, the housing further comprises a first through-hole configured to engage the plunger in the unlocked position, and a second through-hole configured to engage the plunger in the locked position.

In certain embodiments, the soft stop comprises: a keyed distal end feature configured to rotatably engage a complementarily keyed feature on a proximal end of the thumbwheel, the keyed distal end feature being coupled to a longitudinally extending body having a plurality of threads disposed thereon. A slider body is configured to threadedly engage the longitudinally extending body and to translate within the soft stop. A first wave spring and a second wave spring are disposed at opposite ends of the slider body, respectively. In certain embodiments, the thumbwheel is configured to be rotatable even after the slider body abuts the first wave spring or the second wave spring.

A second aspect of the disclosure provides a system comprising: the inserter as described in the first aspect above, and a spinal fusion implant configured to be engaged by the distal end of the inserter. In certain embodiments, the spinal fusion implant may include a threaded connection, configured to threadedly engage with the distal tip of the inserter.

A third aspect of the disclosure provides an inserter for inserting a spinal fusion implant, the inserter comprising: a body comprising an outer shaft; an inner shaft having a distal end configured to releasably engage the spinal fusion implant, and a proximal end, wherein the inner shaft is disposed at least partly within the outer shaft. A thumbwheel is rotatably fixed to the inner shaft, and disposed about the body, wherein the thumbwheel is configured to translate relative to the body in order to allow rotational movement of the thumbwheel about a longitudinal axis of the inserter. The thumbwheel is configured to rotate a first extent about the longitudinal axis in order to move the inserter between an unlocked position, in which the inner shaft is configured to engage and disengage the spinal fusion implant, and a locked position, in which the inner shaft is locked in engagement with the spinal fusion implant. The thumbwheel is further configured to rotate a second extent about the longitudinal axis in order to allow removal of the thumbwheel from the body.

In certain embodiments, the body further comprises a middle body member coupled to the outer shaft, and a proximal body member coupled to the middle body member.

In certain embodiments, the middle body member further comprises a counter torque point.

In certain embodiments, the body further comprises a backing plate and a biasing element affixed to the backing plate, wherein the biasing element is configured to bias the thumbwheel in a distal direction. In certain embodiments, the biasing element comprises a wave spring.

In certain embodiments, the body further comprises a lock button disposed thereon, the lock button being configured to extend radially outward relative to the body, and configured to be depressed in a radially inward direction. The thumbwheel further comprises a first cutout disposed on an inner bore of the thumbwheel, configured to accommodate the lock button in the unlocked position.

In certain embodiments, the thumbwheel further comprises a relief disposed on a distal end surface thereof, the relief being configured to accommodate the lock button when the thumbwheel has been rotated the second extent about the longitudinal axis.

In certain embodiments, the body further comprises a fixed tab disposed thereon, and the thumbwheel further comprises a second cutout disposed on the inner bore thereof, configured to accommodate the fixed tab in the unlocked position.

In certain embodiments, the first cutout is further configured to accommodate the fixed tab in the locked position, and the second cutout is further configured to accommodate the lock button in the locked position.

In certain embodiments, the first cutout and the second cutout are arranged in opposition to one another on the inner bore of the thumbwheel, such that the first and second cutouts are disposed about 180° from one another.

In certain embodiments, the thumbwheel further comprises a radial track disposed on the inner bore thereof, the radial track being in communication with, and disposed distally relative to the first cutout and the second cutout, the radial track being configured to allow the thumbwheel to rotate about the body when the thumbwheel translates in a proximal direction, such that the fixed tab and the lock button are accommodated within the radial track.

In certain embodiments, the inserter further comprises a rotatable tab coupled to the inner shaft at a proximal end thereof, the rotatable tab being rotatable relative to the body and extending through a portion of the body. The tab is rotatably fixed relative to the inner shaft. A first channel extends axially along the inner bore of the thumbwheel, and is configured to accommodate the rotatable tab, wherein the rotatable tab is configured to rotate about a longitudinal axis of the inserter and within the first channel in response to the thumbwheel rotating about the longitudinal axis of the inserter. The inner shaft is configured to rotate in response to the rotating of the rotatable tab.

In certain embodiments, the first channel is open at a distal end thereof to the first cutout.

In certain embodiments, the inserter further comprises a second channel extending axially along the inner bore of the thumbwheel, configured to accommodate the fixed tab when the thumbwheel has rotated the second extent, thereby allowing the thumbwheel to translate distally off an end of the body for removal.

In certain embodiments, the first extent is about 180°, and the second extent is about 90°.

In certain embodiments, the inserter further comprises a cam disposed on the distal end of the inner shaft and configured to engage a cam surface on the spinal fusion implant.

A fourth aspect of the disclosure provides a system comprising: the inserter as described in the third aspect above, and a spinal fusion implant configured to be engaged by the distal end of the inserter. In certain embodiments, the inserter includes a cam disposed on the distal end of the inner shaft, configured to engage a cam surface on the spinal fusion implant.

A fifth aspect of the disclosure provides a method of engaging an implant using an inserter according to the first or the third aspect as described above.

A sixth aspect of the disclosure provides a method of disengaging an implant from an inserter according to the first or the third aspect as described above.

A seventh aspect of the disclosure provides a method for disassembling an inserter according to the first or the third aspect as described above.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIGS. 2A and 2B show side cross sectional views of the portion of the housing in box A of FIG. 1, including a lock in accordance with an embodiment of the invention.

FIG. 2C shows a cross sectional view of the slot profile in the lock button along line C-C of FIG. 2A, in accordance with an embodiment of the invention.

9A-9B show a cylindrical inner member of the thumbwheel, FIG. 9C shows a sleeve or grip configured to be disposed over the cylindrical inner member, and FIG. 9D shows the sleeve or grip disposed over the cylindrical inner member.

FIG. 12A shows portions of the inserter without the thumbwheel present; FIG. 12B shows portions of the inserter with only the cylindrical inner member of the thumbwheel present; and FIG. 12C shows portions of the inserter with the thumbwheel present.

Figure 1:
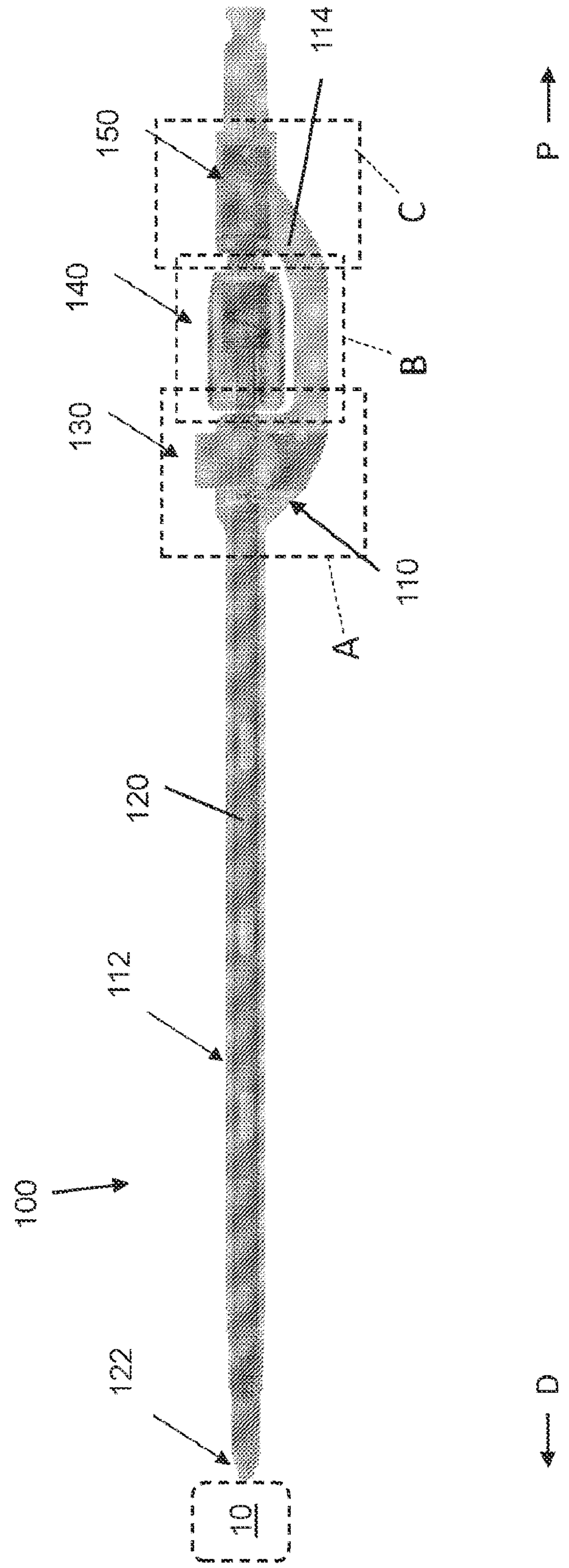
FIG. 1 shows a side cross sectional view of an inserter according to a first embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

As indicated above, aspects of the invention provide inserters for the insertion of spinal fusion implants, methods for engaging an implant using the inserters, methods of disengaging the implant from the inserters, and methods for disassembling the inserters, as well as systems including such inserters and corresponding implants. Such instruments can provide improvements over prior instruments. For example, the instruments can be relevant to ease of engagement and disengagement between the implant and the inserter, ease of actuation, as well as the ability to dismantle the inserter (e.g., before and/or after such procedures) to facilitate cleaning and sterilization of the inserter.

As used herein, the term proximal refers to the direction away from attachment of an element to the subject, shown in FIG. 1 as direction P, while use of the term distal refers to the direction opposite the proximal direction and toward attachment of an element to the subject, shown in FIG. 1 as direction D.

Referring generally to FIGS. 1-5, a first example inserter 100 is provided for use in inserting a spinal fusion implant 10 into an intervertebral space in a spine of a patient.

Figure 5:
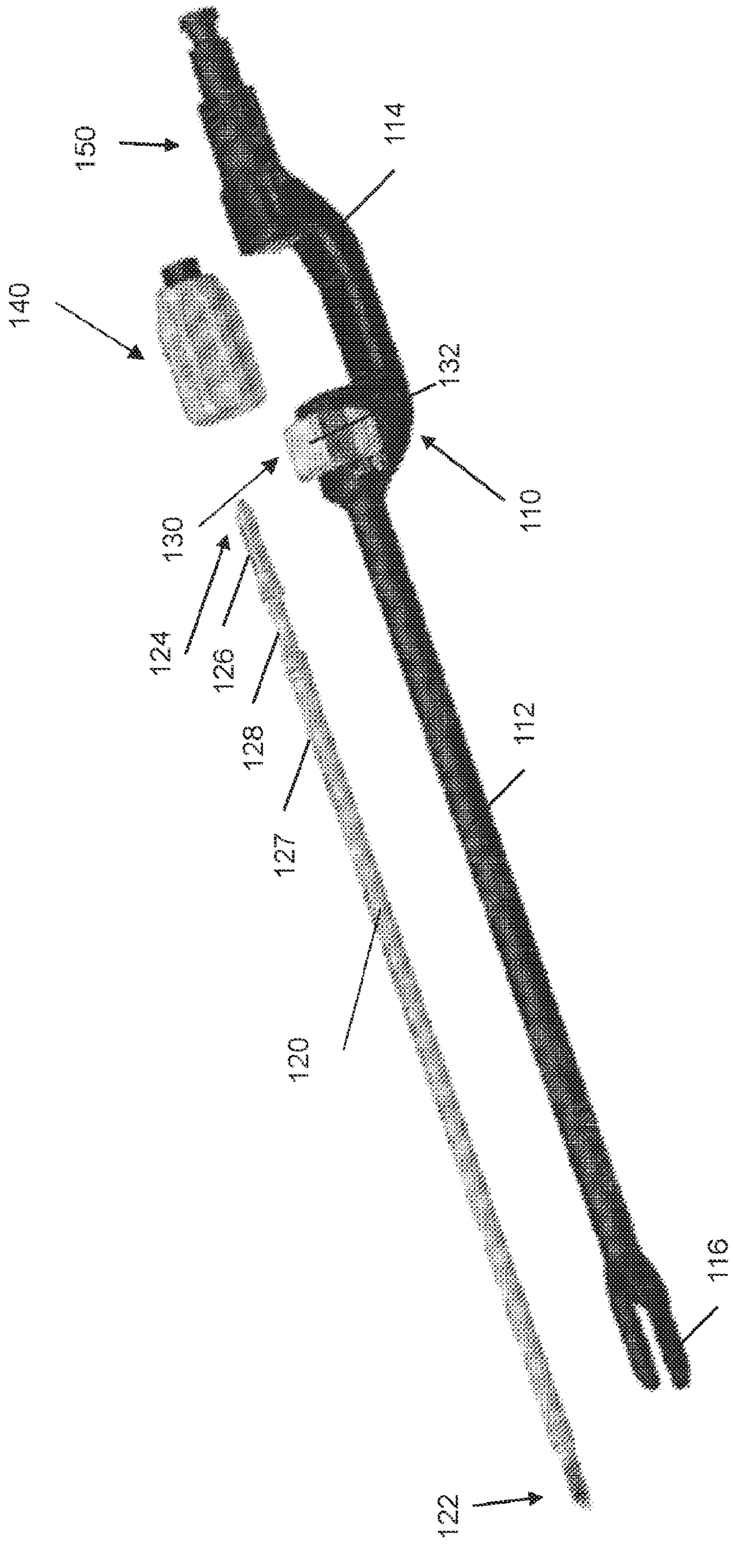
FIG. 5 shows an exploded perspective view of the inserter of FIG. 1 in accordance with an embodiment of the invention.

As shown in FIGS. 1 and 5, inserter 100 may include a housing 110. Housing 110 may include a proximal member 114 and a housing shaft 112 extending distally from the proximal member, to a distal end 116. In various embodiments, proximal member 114 may be substantially "C" shaped or otherwise adapted to accommodate a thumbwheel 140. Housing shaft 112 and proximal member 114 may be a single unitary structure or may include two or more members that are coupled together to form housing 110.

As shown in FIG. 1, an inner shaft 120, having a distal end 122 and a proximal end 124, is configured to be disposed at least partially within housing shaft 112 when assembled for use. The distal end 122 is configured to releasably engage the spinal fusion implant 10. In certain embodiments, the distal end 122 of inner shaft 120 may be threaded, and may be configured to engage complementary threads on the spinal fusion implant 10. For example, distal end 122 may include a male threaded feature, and spinal fusion implant 10 may include a female threaded feature. Thus, rotation of inner shaft 120 in a first direction (e.g., clockwise or counterclockwise) may result in engagement (e.g., threaded engagement) of distal tip 122 of inner shaft 120 with implant 10, while rotation of inner shaft 120 in another direction may result in disengagement of distal tip 122 of inner shaft 120 from implant 10. In addition to rotating within housing shaft 112, inner shaft 120 is configured to translate relative to housing shaft 112.

The thumbwheel 140 is configured to be rotatably fixed to the inner shaft 120, for example, thumbwheel 140 may be rotatably fixed to the proximal end 124 of inner shaft 120. Thumbwheel 140 is configured to provide a user (e.g., a surgeon, medical professional, or operating room technician) with a readily accessible means of actuating rotation of the inner shaft 120. Thumbwheel 140 is configured to rotate about a longitudinal axis of the inserter 100, thereby causing the inner shaft 120 to rotate. As discussed above, rotation of the thumbwheel 140 in a first direction is configured to cause the distal end 122 of the inner shaft 120 to engage the spinal fusion implant 10, and rotation of the thumbwheel 140 in a second direction is configured to cause the distal end 122 of the inner shaft 120 to disengage from the spinal fusion implant 10. Rotation of inner shaft 120 may directly correspond to the degree of rotation of thumbwheel 140.

A lock 130 may be engaged with the inner shaft 120 (e.g., at a proximal end 124 thereof). The lock 130 is configured to move between a locked position and an unlocked position. In the locked position, the inner shaft 120 (e.g., the proximal end 124 of inner shaft 120) is disposed within and rotatably fixed to the thumbwheel 140. In the unlocked position, the inner shaft 120 and the thumbwheel 140 are separable from one another (e.g., they can be disassembled). In particular, in the unlocked position, the lock 130 is configured to disengage from inner shaft 120, allowing inner shaft 120 to translate distally within housing shaft 112, causing the proximal end 124 of inner shaft 120 to disengage from the thumbwheel 140. In this state, inner shaft 120 is configured to translate distally and ultimately to be removed from housing shaft 112 from the distal end 116 thereof.

A soft stop 150 is configured to provide one or more of audible and or tactile feedback to a user to indicate that the spinal fusion implant 10 is fully disengaged from the distal end of the inner shaft 120, while still allowing further rotation of the thumbwheel 140.

Figure 3A:
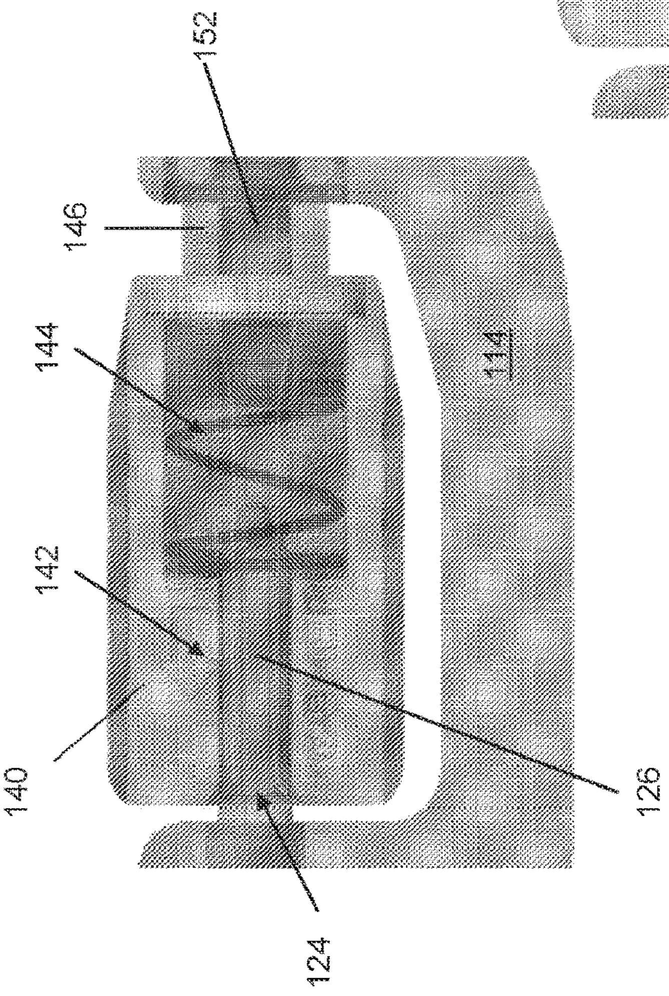
FIGS. 3A and 3B show side cross sectional views of the portion of the housing in box B of FIG. 1, including a thumbwheel in accordance with an embodiment of the invention.
Figure 3B:
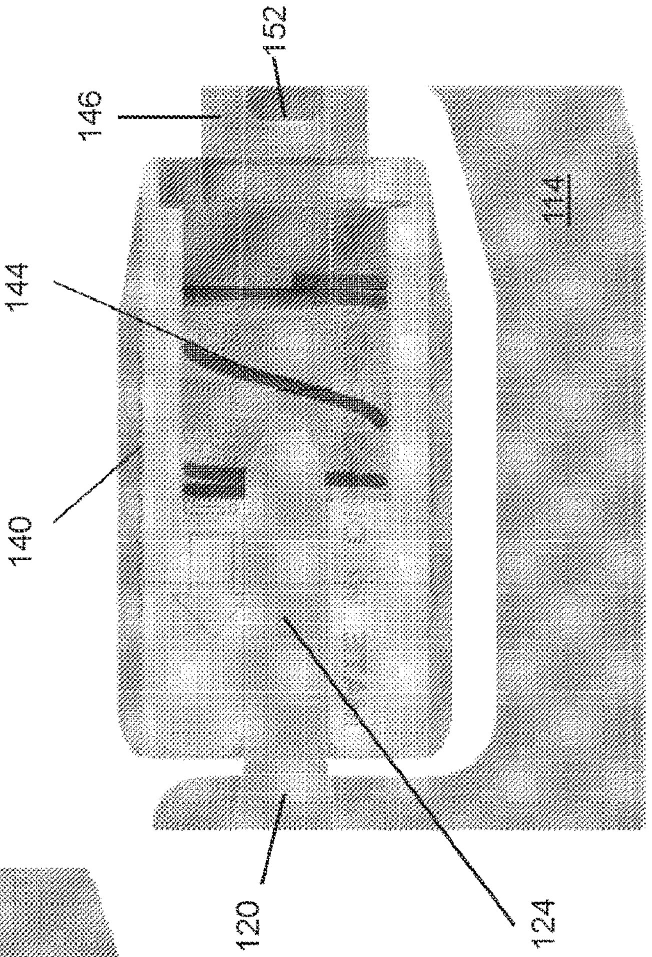

Turning to FIGS. 3A-3B, aspects of thumbwheel 140 of inserter 100 are illustrated. As shown, the proximal end 124 of the inner shaft 120 may include a keyed feature 126, while the distal end thumbwheel 140 may include a corresponding keyed feature 142. Keyed feature 142 may provide a complementary fit with the corresponding keyed feature 126 on the inner shaft 120 (e.g., on the proximal end 124 thereof) such that rotation of thumbwheel 140 drives rotation of inner shaft 120. In various examples, keyed feature 126 and keyed feature 142 may fit together in a male/female relationship. Keyed feature 126 may have a cross sectional shape of any non-circular geometry such as rectangle, square, pentagon, hexagon, octagon, or star having any number of points, configured to transfer torque between thumbwheel 140 and inner shaft 120. In the example illustrated in FIG. 3A, keyed feature 126 has a hexagonal cross sectional shape, and keyed feature 142 includes an axially extending channel open to the distal end of the thumbwheel 140, the axially extending channel having a hexagonal cross sectional shape. Keyed feature 142 may have a cross sectional shape that is complementary to, and configured to receive keyed feature 126 with a close fit providing a rotational fixation and torque transfer between inner shaft 120 and thumbwheel 140.

Thumbwheel 140 may include a biasing element 144 disposed within the thumbwheel, which may be configured to bias the thumbwheel 140 in a distal direction. In the locked position, in which the housing 110, inner shaft 120, and thumbwheel 140 are locked together, this biasing of thumbwheel 140 in the distal direction (e.g., toward inner shaft 120) contributes to the maintenance of the locked position and the contact between thumbwheel 140 and inner shaft 120 at keyed features 142, 126.

Thumbwheel 140 is configured to translate proximally, against the force of the biasing element 144. Such translation in the proximal direction causes compression of biasing element 144, and allows thumbwheel 140 to translate in the proximal direction relative to inner shaft 120. When thumbwheel 140 has translated a sufficient distance in the proximal direction, the proximal end 124 of inner shaft 120 is no longer constrained within keyed feature 142 of thumbwheel 140. Proximal end 124 of inner shaft 120 may then disengage from thumbwheel 140. When proximal end 124 of inner shaft 120 has exited keyed feature 142 at the distal end of thumbwheel 140, the distal end of thumbwheel 140 is configured to move radially outward relative to the longitudinal axis of the inserter 100. Disassembly of inserter 100 may then occur, subject to operation of the lock 130 as described further herein: inner shaft 120 can be removed via the distal end 116 of housing shaft 112, and thumbwheel 140 can be removed by pulling thumbwheel 140, distal end first, away from the longitudinal axis of the inserter and off of housing 110.

Turning to FIGS. 2A and 2B, as discussed above, inserter 100 may further include a lock 130, which is configured to lock retain an axial position of inner shaft 120 relative to housing 110.

As shown in FIGS. 2B and 5, inner shaft 120 may have a first diameter 127 along a portion of the shaft. Inner shaft 120 may further include a portion having a second diameter 128 that is reduced, or smaller than the first diameter 127. The portion having the reduced diameter 128 may be disposed between portions having the first diameter 127 in both proximal and distal directions. This portion having the reduced diameter 128 may be configured to interact with a lock button 132 to form the lock 130.

Lock button 132 may be disposed on housing 110, and may be movable in a direction substantially perpendicular to the longitudinal axis of the inserter 100. The lock button 132 may include a slot 134 disposed therein, through which inner shaft 120 passes or extends. The slot 134 may be configured to engage the portion of inner shaft 120 that includes the second, smaller diameter 128. To this end, slot 134 may include an irregular cross sectional shape (FIG. 2C) configured to accommodate the first diameter 127 at one end, and the second, reduced diameter 128 at the other end. When the lock 130 is in the locked position, the lock button 132 is depressed (e.g., the outer surface of the lock button is substantially flush with the outer surface of housing 110) and a first end 131 of the slot 134 provides a close fit with the portion of the inner shaft having the reduced diameter 128. Thus, when lock button 132 is depressed, the first end 131 of slot 134, which has a diameter configured to provide a close fit around the second, reduced diameter 128 portion of inner shaft 120, is pressed down onto inner shaft 120, slot 134 engages the portion of inner shaft 120 having the reduced diameter 128. In this manner, the narrower first end 131 of slot 134 engages reduced diameter portion 128 of inner shaft 120, and prevents translation in either a proximal or distal direction. In this position, the portions of inner shaft 120 having the first diameter 127 that are both proximal and distal of reduced diameter portion 128 are not accommodated within first end 131 of slot 134, through which inner shaft 120 passes.

When lock 132 is in the unlocked position, shown in FIGS. 2A and 2B, the outer surface of the lock button 132 is raised relative to the outer surface of the housing 110, thus translating lock button 132 and slot 134 upward. In this position, the second end 133 of slot 134 is aligned with inner shaft 120. The second end 133 of slot 134 is shaped and dimensioned to accommodate the larger diameter 127 of inner shaft 120. Thus, when lock button 132 is raised, inner shaft 120 is accommodated through slot 134 along its full length, including the portions having the first, larger diameter 127. In this position, the inner shaft 120 may translate without restriction.

Lock 130 may further include a track 136 extending within the lock button in a direction parallel to the direction in which the lock button 132 is movable. A pin 138 may be disposed within track 136. Track 136 and pin 138 may be configured to further define and limit the motion of lock button 132. A plunger 135 may further be disposed within the housing 110, and be configured to engage the lock button 132 in the locked position and the unlocked position. A spring 137 may be configured to engage the plunger 135, and a screw 139 may further be configured to maintain a position of the plunger and the spring. Housing 110 may further include a first through-hole 118*a* configured to engage the plunger 135 in the unlocked position, and a second through-hole 118*b* configured to engage the plunger 135 in the locked position. The inserter 100 can be manually or automatically moved from the locked position (e.g., lock button depressed) to the unlocked position (e.g., lock button raised). For instance, a user can manually change the inserter 100 from the locked position to the unlocked position.

Figure 4A:
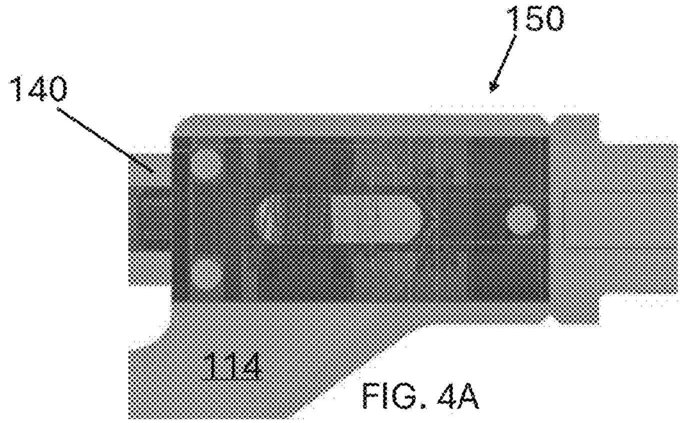
FIGS. 4A and 4B show side cross sectional views of the portion of the housing in box C of FIG. 1, including a soft stop in accordance with an embodiment of the invention.
Figure 4B:
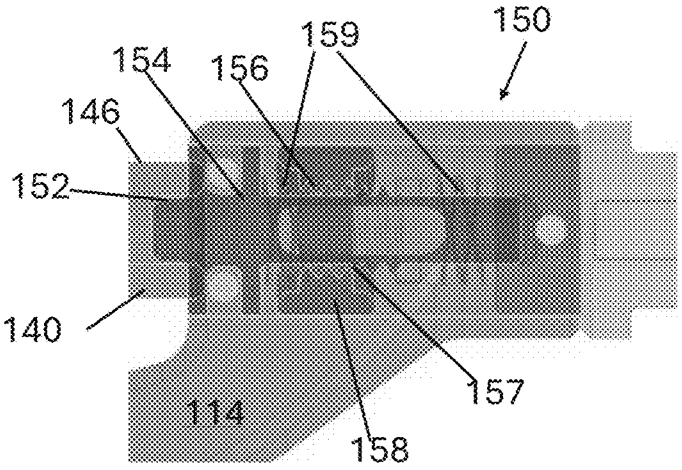

Turning next to FIGS. 4A-4B, the inserter 100 may further include a soft stop 150. As previously mentioned, soft stop 150 may be configured to provide audio and/or tactile feedback to a user when the inner shaft 120 has fully disengaged from the implant 10 (FIG. 1). Thumbwheel 140 may include a keyed feature 146 disposed on a proximal end thereof, which may be configured to rotatably engage a complementarily keyed feature 152 on a distal end of the soft stop 150. For example, keyed features 146 and 152 may engage with one another in female/male correspondence. Keyed feature 152 may have a cross sectional shape of any non-circular geometry such as, e.g., rectangle, square, pentagon, hexagon, octagon, or star having any number of points, configured to transfer torque between thumbwheel 140 and body 154 of soft stop 150. Keyed feature 152 may be coupled to a body 154 extending axially in a proximal direction. The body 154 may include a plurality of threads 156 disposed on an outer surface thereof. A slider body 158 may be disposed within soft stop 150, and may include a threaded aperture 157 configured to threadedly engage threads 156 on the longitudinally extending body 154. A pair of biasing members 159 may be disposed at opposite ends of soft stop 150, on either side of slider body 158.

In use, as thumbwheel 140 including keyed feature 146 rotates in the second direction to disengage distal tip 122 from implant 10, body 154 rotates in response to the rotation of thumbwheel 140. Body 154 is fixed in its axial position, but rotates relative to slider body 158. As a result of the threaded engagement between threads 156 on body 154, and the threaded aperture 157 of slider body 158, slider body is configured to translate along the interior bore of soft stop 150, driven by the rotating threads of body 154. As thumbwheel 140 is rotated, slider body 158 is configured to translate either proximally or distally, depending on the direction in which thumbwheel 140 is rotated. Eventually, slider body 158 translates to the proximal or distal end of soft stop 150, and contacts a biasing member 159. Each biasing member 159 may be, e.g., a wave spring. This contact between slider body 158 and a biasing member 159 is configured to provide tactile and/or audible feedback to the user.

The axial length of soft stop 150 is configured such that when the thumbwheel has been rotated a sufficient number of times to generate the audible and/or tactile feedback as described above, the inner shaft 120 can be understood by the user to be completely disengaged from implant 10. This feedback allows the user to, e.g., withdraw the inserter 100 from the patient with confidence that the implant 10 is not still engaged, and will not be inadvertently moved from its position by the withdrawal of inserter 100. This feedback also allows the user to withdraw the inserter 100 from the patient promptly after disengaging from the implant 10, without rotating the thumbwheel 140 an unnecessary additional number of times beyond the point of disengagement with the implant 10 in an effort to avoid inadvertent repositioning of the implant 10. Soft stop 150 may be configured such that thumbwheel 140 continues to be rotatable even after slider body 158 has contacted and/or abuts one of biasing members 159.

In addition to the inserter 100 described above, it is also considered that in another embodiment, a system is provided for use in a spinal fusion procedure. The system may include the inserter 100 substantially as described herein, together with a spinal fusion implant 10 (FIG. 1). Suitable spinal fusion implants are known in the art. Example spinal implants that can benefit from instruments herein include: U.S. Pat. No. 10,675,158 (application Ser. No. 16/010,405, filed Jun. 16, 2018); the implant described by U.S. Pat. No. 10,390,960 (application Ser. No. 15/635,087, filed Jun. 27, 2017); U.S. Pat. No. 9,730,802 (application Ser. No. 14/597,085, filed Jan. 14, 2015); and the spinal implant described by U.S. Pat. No. 9,180,021 (application Ser. No. 14/314,823, filed Jun. 25, 2014), the contents of which are incorporated by reference herein in their entirety for any and all purposes.

Also provided herein is an exemplary method of use of inserter 100. According to a first step, inserter 100 is provided. Inserter 100 may be in a disassembled condition, and if so, it may be assembled. Such assembly may include placing keyed feature 146 of thumbwheel 140 on keyed feature 152 of soft stop 150, and bringing thumbwheel 140 into alignment with the longitudinal axis of inserter 100. Inner shaft 120 may then be inserted in a proximal direction into housing shaft 112, such that proximal end 124 engages with thumbwheel 140. In a second step, thumbwheel 140 may be rotated in a first direction to engage implant 10. In a third step, the lock button may be pressed to lock the axial position of inner shaft 120, and the rotational position of inner shaft 120 and thumbwheel 140. In a fourth step, the implant 10 may be inserted through an incision and placed in a desired location in a patient, e.g., in an intervertebral space. In a fifth step, the inserter 100 may be unlocked, causing the lock button to extend upward such that it is no longer flush with the housing surface. In a sixth step, the thumbwheel 140 may be rotated in a second direction that is opposite the first direction, causing the distal tip 122 of the inner shaft 120 to disengage from implant 10. In a seventh step, the rotation may be discontinued after feedback is received by the user from soft stop 150. In an eighth step, inserter 100 may be withdrawn from the patient. In a ninth step, the inner shaft may be removed from inserter 100 in a distal direction. Finally, in a tenth step, the thumbwheel, no longer constrained by the proximal end of the inner shaft, may be removed from housing 110. Inserter 100 may then be cleaned or sterilized in its disassembled condition.

Figure 6:
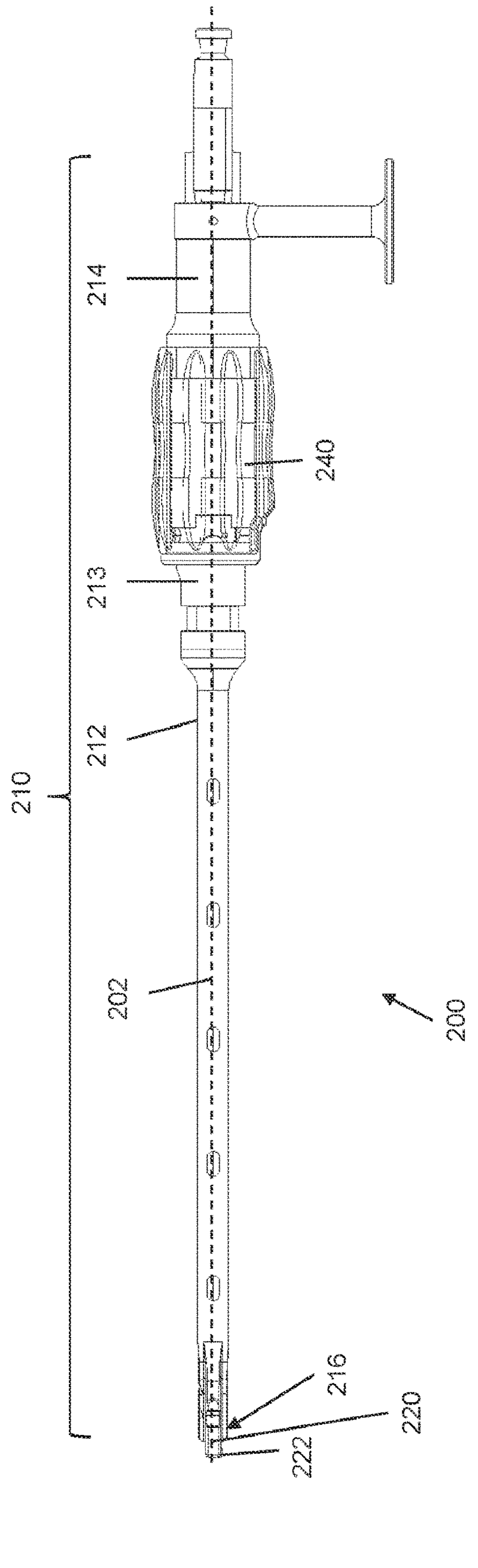
FIG. 6 shows a side view of an inserter according to a second embodiment of the invention.
Figure 7:
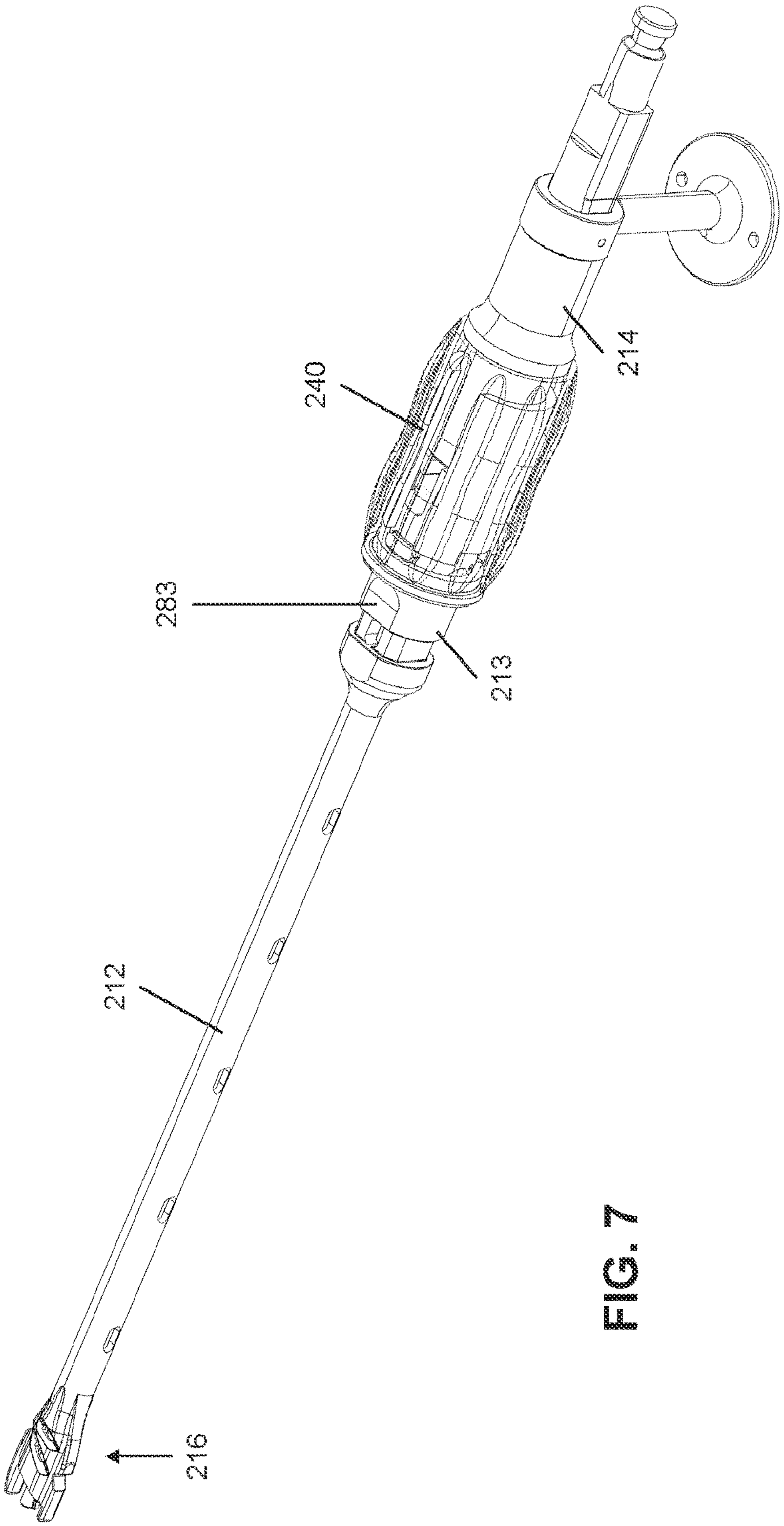
FIG. 7 shows a perspective view of an inserter according to the embodiment of FIG. 6.
Figure 8:
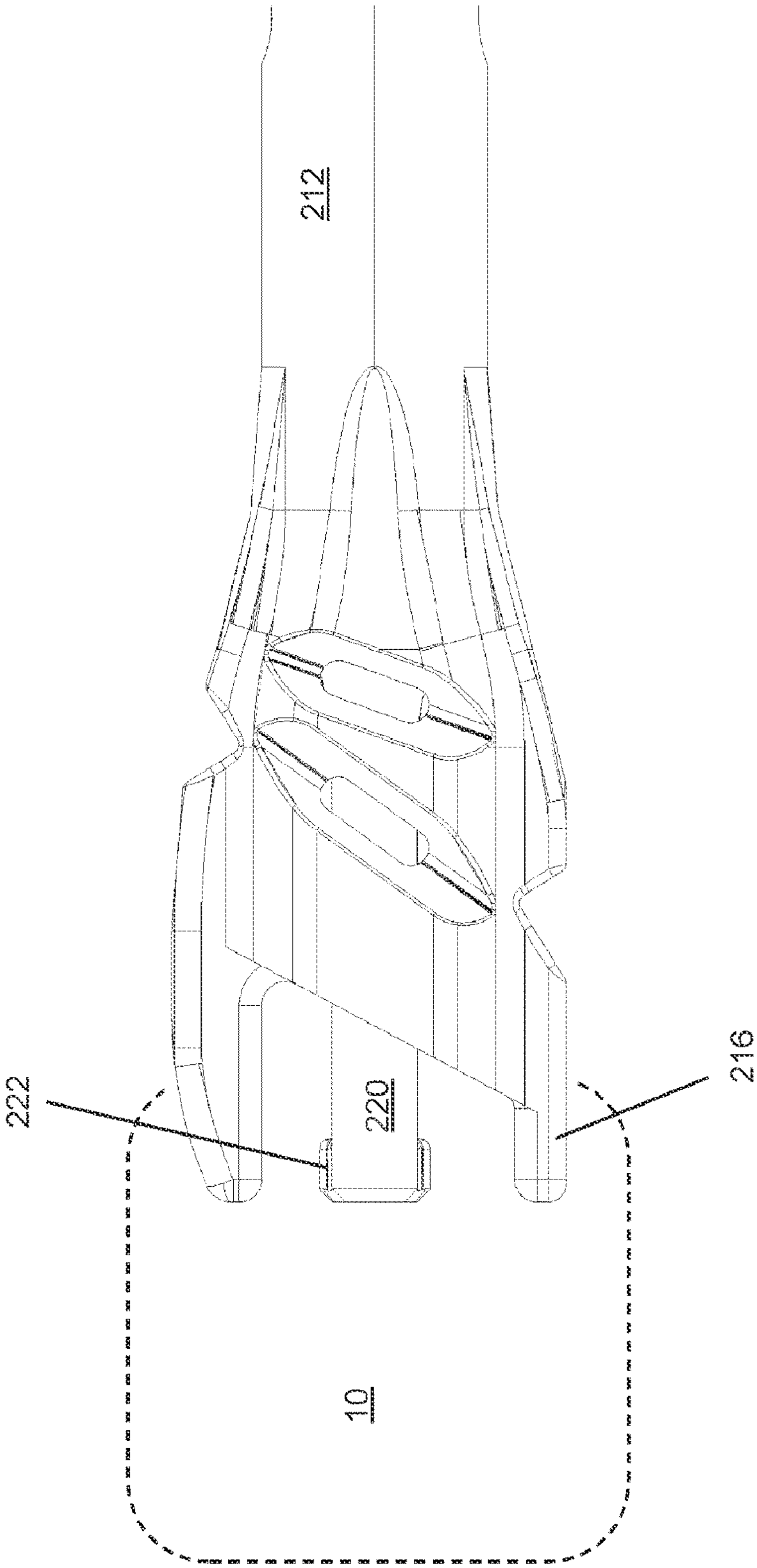
FIG. 8 shows a top view of a distal portion of an inserter according to the embodiment of FIG. 6.

With reference to FIGS. 6-31, an inserter 200 according to a further embodiment is described herein. As shown in FIG. 6, an inserter 200 for inserting a spinal fusion implant 10 (FIG. 8) is disclosed. Inserter 200 may include a body 210 including an outer shaft 212, and an inner shaft 220 disposed at least partly within the outer shaft 212. Inner shaft 220 may include a distal end 222, details of which are illustrated in FIG. 8. Distal end 222 of inner shaft 220 may extend from distal end 216 of outer shaft 212, and may be configured to releasably engage the spinal fusion implant 10 (see FIG. 8). In certain embodiments, inner shaft 220 may include a cam disposed on the distal end 222 thereof, the cam being configured to engage a cam surface on the spinal fusion implant 10. Inner shaft 220 may further include a proximal end 224 (see FIGS. 11A-11B).

With continued reference to FIG. 6, body 210 of inserter 200 may include more than one body member. As noted, body 210 may include a distal body member, which includes an outer shaft 212. Body 210 may further include a middle body member 213 coupled to a proximal end of the outer shaft 212. Middle body member 213 may in turn be coupled at its proximal end to a proximal body member 214. In certain embodiments, features of body 210 may be disposed on particular body members, e.g., a counter torque point 283 may be provided on middle body member 213 (FIG. 7), and a biasing member 282 (FIG. 13) may be provided on proximal body member 214, as described further herein.

Inserter 200 may further include a thumbwheel 240 that is rotatably fixed to the inner shaft 220, e.g. at a proximal end 224 thereof, and may be disposed about the body 210. Thumbwheel 240 may provide a user with a means of actuating rotation and/or translation of inner shaft 220 that is easy to access and manipulate.

Thumbwheel 240 may include a plurality of relief features on an inner bore surface 267 thereof, which may be configured to interact with features of body 210 to provide inserter 200 with a number of functionalities as described herein. For example, as facilitated by the features of the inner bore surface 267 of thumbwheel 240 and of body 210, the thumbwheel 240 may be configured to translate relative to the body 210, in order to permit or allow rotational movement of the thumbwheel 240 about a longitudinal axis 202 of the inserter 200. In particular, the thumbwheel 240 may translate in a proximal direction in order to permit rotational movement of the thumbwheel 240 about the longitudinal axis 202 of the inserter 200.

Thumbwheel 240 may further be configured to rotate about the longitudinal axis 202 in order to move the inserter 200 between an unlocked position, in which the inner shaft 220 is configured to engage and disengage the spinal fusion implant 10, and a locked position, in which the inner shaft 220 is locked in engagement with the spinal fusion implant, and the inner shaft 220 and thumbwheel 240 are rotationally locked. In particular, translation of thumbwheel 240, e.g., in a proximal direction as described above, may permit thumbwheel 240 to be rotated a first extent, for example about 180° about the longitudinal axis 202, in order to move the inserter 200 from the unlocked position to the locked position, or vice versa. In other embodiments (e.g., embodiments having a double cam disposed at the distal tip 222 of inner shaft 220) the first extent may be about 90°. In the latter embodiment, other angular and spatial relationships as disclosed herein may be adjusted in order to accommodate.

Upon proximal translation, thumbwheel 240 may further be configured to rotate a second extent about the longitudinal axis 202, for example about 90° F.rom the unlocked position, to a removal position in which the thumbwheel 240 is configured to be removed from the body 210. For example, thumbwheel 240 may be removed from body 210 by sliding thumbwheel 240 off a distal end of body 210.

As noted above, thumbwheel 240 may include a plurality of relief features on an inner bore surface 267 thereof, which are configured to interact with corresponding features on body 210 as described further herein to provide certain functions of thumbwheel 240 and inserter 200. With reference to FIGS. 9A-9D, these features of thumbwheel 240, including, e.g., first cutout 260, second cutout 262, relief 264, radial track 266, channel 268, and channel 269, may include reliefs cut through a partial thickness of a unitarily formed thumbwheel body, or alternatively, may be full or partial thickness features cut through a cylindrical inner member 261 configured to be disposed within a sleeve or grip member 263 to collectively form thumbwheel 240. In one embodiment shown in FIGS. 9A-9D, FIGS. 9A-9B illustrate a cylindrical inner member 261 including various features described herein, while FIG. 9C illustrates a sleeve or grip 263 configured to be disposed over cylindrical inner sleeve 261. FIG. 9D illustrates sleeve or grip 263 disposed over cylindrical inner member 261 to collectively form thumbwheel 240.

Referring back to FIG. 9A, thumbwheel 240 may include a first cutout 260 disposed on an inner bore 267 of the thumbwheel 240. First cutout 260 may have a depth and a width configured to accommodate the size and dimensions of a lock button 286 (see FIGS. 13-14) when inserter 200 is in the unlocked position. The lock button 286 may be disposed on body 210, e.g., middle body member 213, as described further herein. As shown in FIG. 9B, thumbwheel 240 may further include a second cutout 262, also disposed on the inner bore 267 of thumbwheel 240. Second cutout 262 may have a depth and a width configured to accommodate the size and dimensions of a fixed tab 284 disposed on body 210, e.g., on middle body member 213, when inserter 200 is in the unlocked position (see FIG. 15). First cutout 260 and second cutout 262 may have substantially similar dimensions and shapes, and may be spaced about 180° apart along the circumference of thumbwheel 240, at a common axial position. This arrangement allows first cutout 260 to accommodate the fixed tab 284, and the second cutout 262 to accommodate the lock button 286 when the thumbwheel 240 has been rotated 180° from the unlocked position to the locked position (see, e.g., FIGS. 22-23).

As noted, a lock button 286 (see, e.g., FIGS. 11A and 12A) may be disposed on body 210, e.g., on middle body 213, and may extend radially outward therefrom. Lock button 286 is configured to interact with inner shaft 220 to retain an axial position of inner shaft 220 relative to body 210, and of thumbwheel 240 relative to body 210. Lock button 286 may be movable in a direction substantially perpendicular to the longitudinal axis 202 of the inserter 200, into and out of a recess 215 in body 210 (e.g., in middle body member 213).

Lock button 286 is further configured to prevent rotation of thumbwheel 240 in certain configurations through interaction with first and second cutout 260, 262. A fixed tab 284 may further be disposed on body 210 (e.g., on middle body 213). Fixed tab 284 (see FIG. 11B) may also extend radially outward relative to body 210, and may be of a shape and dimension substantially similar to that of lock button 286.

Thumbwheel 240 may further include a relief 264 (see FIGS. 9B, 9D) disposed on a distal end surface thereof. Relief 264 may be in the form of an indentation or recess in the distal end surface of thumbwheel 240. Relief 264 may be configured to accommodate the lock button 286 when the thumbwheel 240 has been rotated the second extent around the longitudinal axis 202, e.g., about 90° (see FIG. 24). When lock button 286 is accommodated within relief 264, rotation of thumbwheel 240 is prevented by interaction between the raised lock button 286 and the edges of relief 264.

Figure 9A:
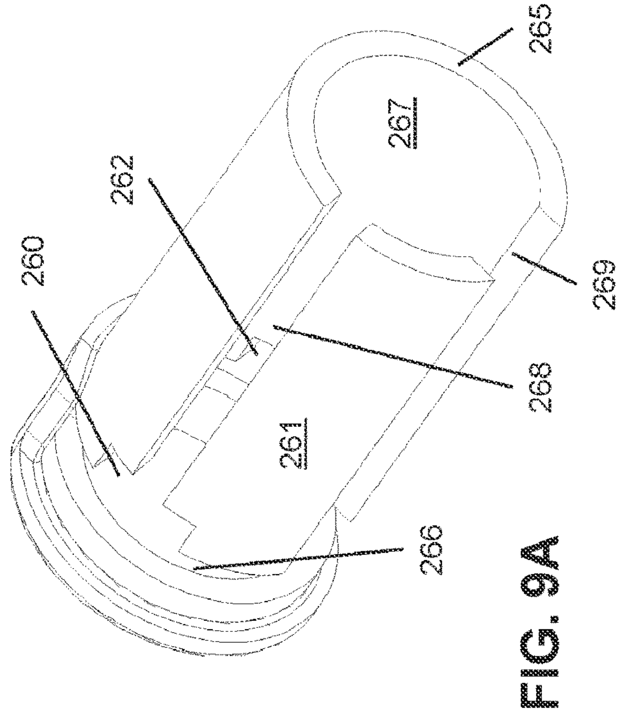
FIGS. 9A-9D show perspective views of portions of a thumbwheel of the inserter of FIG. 6. In particular, FIGS.
Figure 9B:
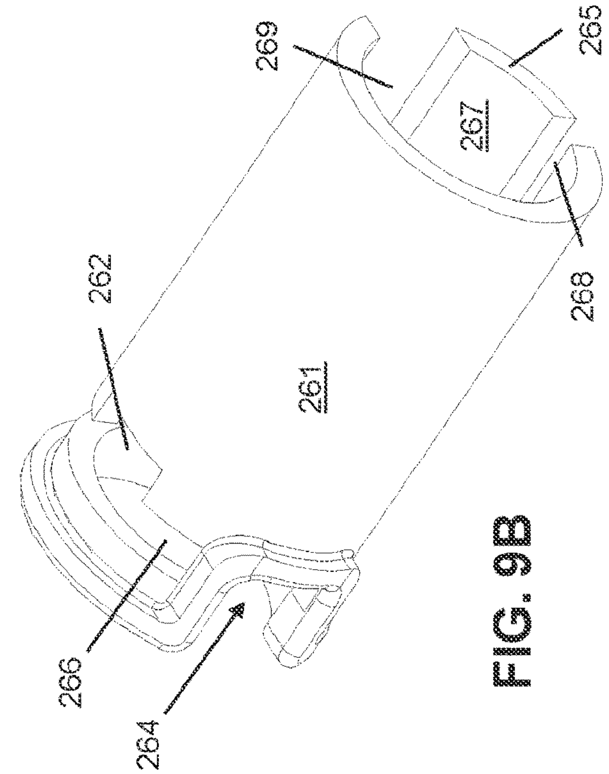
Figure 9C:
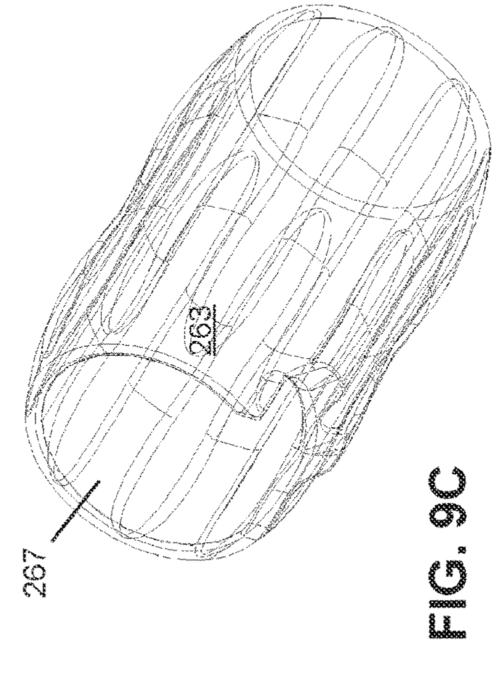
Figure 9D:
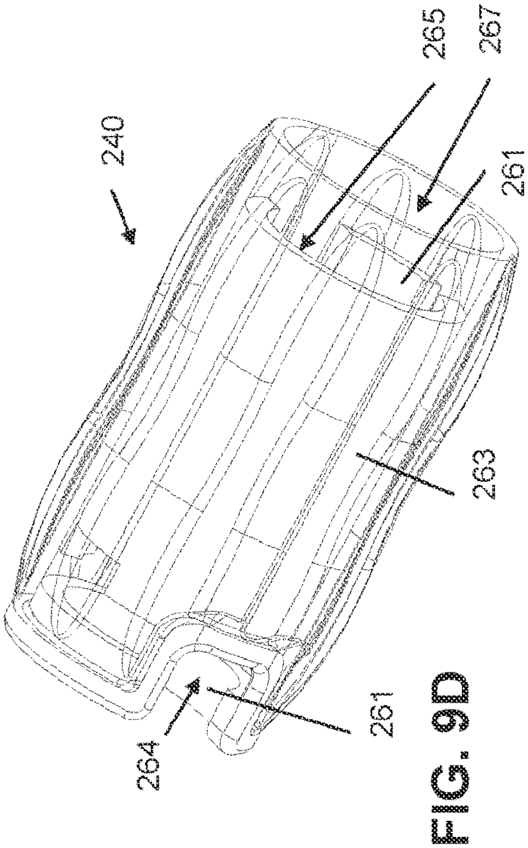
Figure 10B:
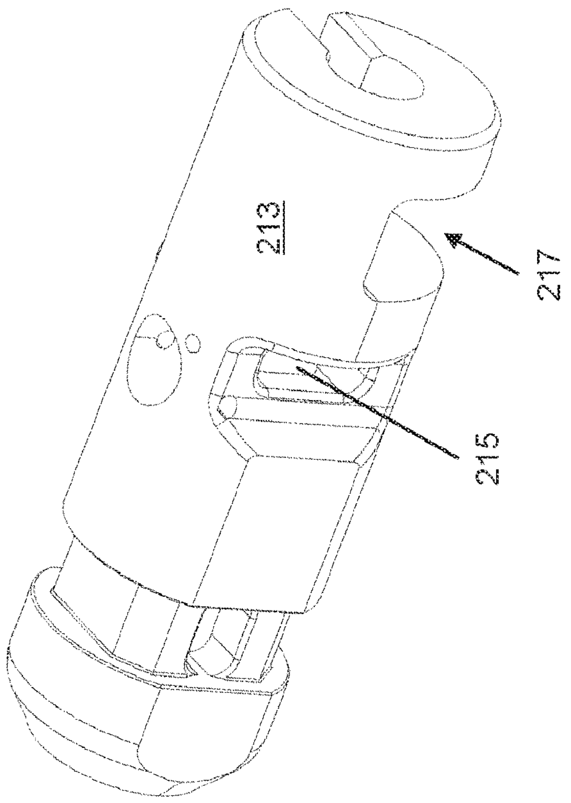
FIGS. 10A-10B show perspective views of a portion of the body of the inserter according to the embodiment of FIG. 6.
Figure 10A:
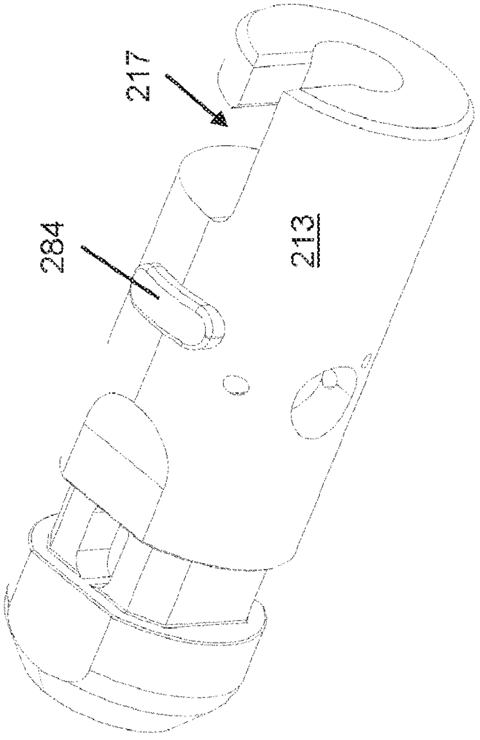

Thumbwheel 240 may further include a radial track 266, shown in FIGS. 9A-9B, which may be in the form of a radially oriented track or channel extending circumferentially about the inner surface 267 of thumbwheel 240. Radial track 266 may be in communication with both of first and second cutouts 260, 262, such that radial track 266 provides a continuous passage between first cutout 260 and second cutout 262, along which fixed tab 284 and lock button 286 may travel as thumbwheel 240 is rotated. Radial track 266 may be disposed distally relative to the first and second cutouts 260, 262. As a result, features such as fixed tab 284 and lock button 286, which are disposed within cutouts 260, 262 at rest, are configured to enter radial track 266, and thus confer on thumbwheel 240 the freedom to rotate, when thumbwheel 240 is translated proximally. Radial track 266 thus permits thumbwheel 240 to rotate about the body 210 when the thumbwheel 240 has translated in a proximal direction, such that the fixed tab 284 and the lock button 286 are accommodated within the radial track 266.

With continued reference to FIGS. 9A-9B, a first channel 268 axially extends along the inner bore 267 of thumbwheel 240. First channel 268 may be oriented and located such that first channel 268 is open at a distal end thereof to a base surface defining a depth of the first cutout 260. First channel 268 may extend proximally therefrom. First cutout 260 and first channel 268 may therefore be in communication with one another. First channel 268 is configured to accommodate a rotatable tab 288 (see FIG. 11A, 11B), which is disposed on body 210, e.g., on middle body 213.

Figure 11A:
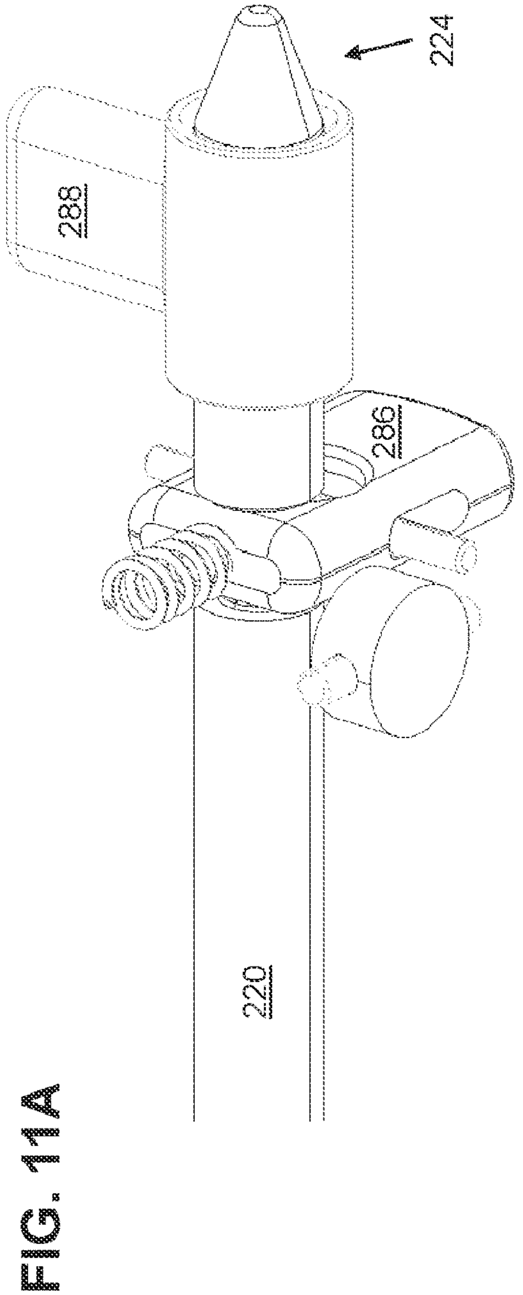
FIG. 11A shows a perspective view of the proximal end of the inner shaft of the inserter according to the embodiment of FIG. 6.
Figure 11B:
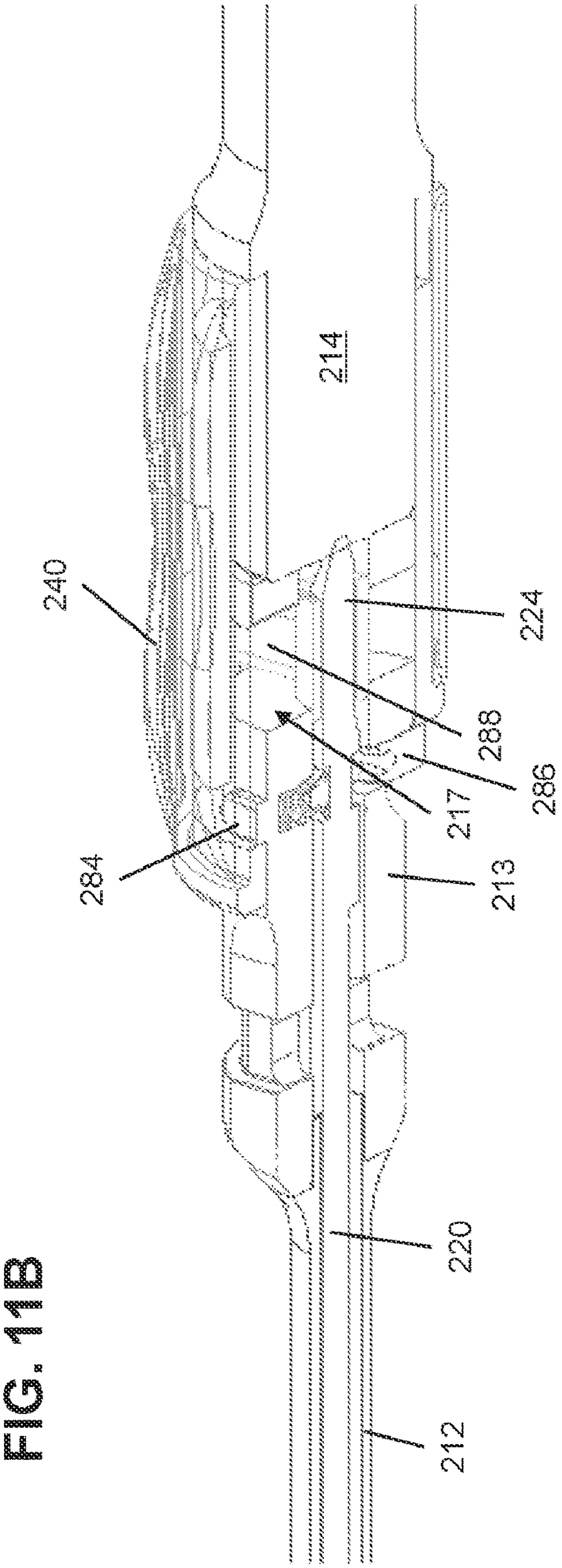
FIG. 11B shows a cross sectional view of a portion of the inserter according to the embodiment of FIG. 6.
Figure 12A:
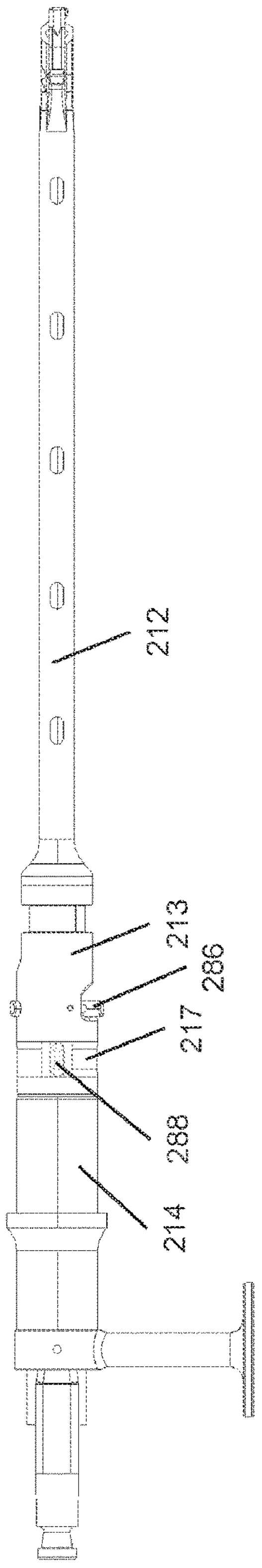
FIGS. 12A-12C show rear views of portions of the inserter according to the embodiment of FIG. 6. In particular.

As shown in FIGS. 11A and 11B in greater detail, rotatable tab 288 may be coupled to proximal end 224 of inner shaft 220, such that rotatable tab 288 is rotatably fixed relative to the inner shaft 220. Rotatable tab 288 may extend radially outward from inner shaft 220, and rotation of tab 288 around inner shaft 220 may be configured to cause the inner shaft 220 to rotate a corresponding extent. As shown in FIG. 12A, body 210, e.g., middle body member 213, may be disposed over the proximal end 224 of inner shaft 220, and over rotatable tab 288 as well. Middle body member 213 may include a track 217 (see FIGS. 10A, 10B, 12A) through which rotatable tab 288 extends, to permit engagement with thumbwheel 240. Track 217 may extend a partial extent around a circumference of the middle body 213. For example, track 217 may extend about 180° around the circumference of the middle body, thereby providing tab 288 with a range of motion of about 180°, while axially constraining tab 288.

Figure 12B:
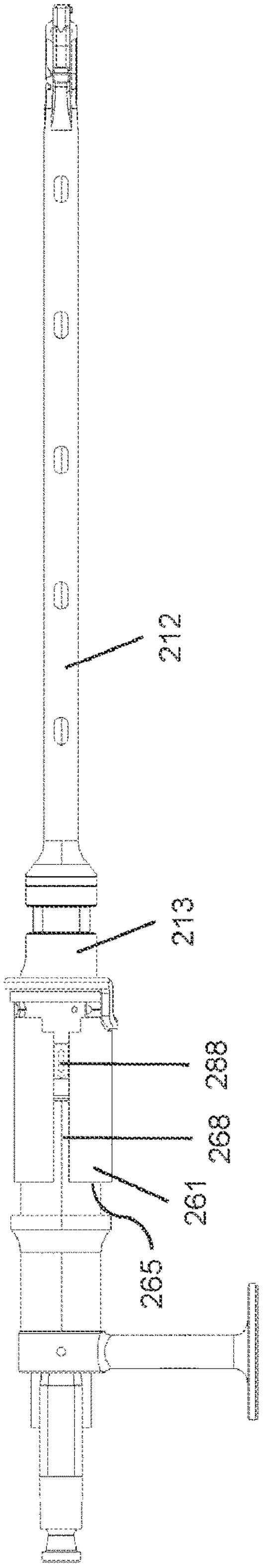
Figure 12C:
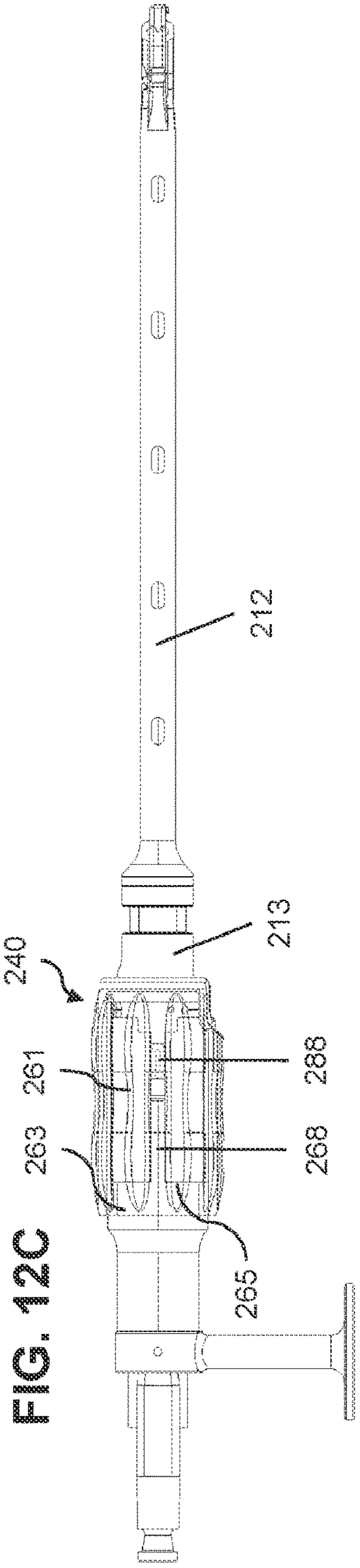

As shown in FIG. 12B, rotatable tab 288 may be accommodated within first channel 268 of thumbwheel 240. The interaction between first channel 268 and tab 288 provide a rotational connection between thumbwheel 240 and inner shaft 220. Rotatable tab 288 is restrained within, and rotatably fixed relative to first channel 268. Rotatable tab 288 is thus configured to rotate within track 217 about the longitudinal axis 202 of body 210, in response to rotation of the thumbwheel 240 about longitudinal axis 202. In this manner, rotation of thumbwheel 240, results in rotation of rotatable tab 288, which in turn causes rotation of inner shaft 220. FIG. 12C illustrates the inserter in the same position shown in FIG. 12B, with the sleeve or grip 263 disposed over cylindrical inner member 261.

Referring back to FIGS. 9A and 9B, thumbwheel 240 may further include a second channel 269 that extends axially along the inner bore 267 of thumbwheel 240. Second channel 269 may be sized and dimensioned to accommodate the fixed tab 284 when the thumbwheel has rotated the second extent, e.g. about 90°, thereby allowing translation of the thumbwheel 240. In particular, the accommodation by second channel 269 of fixed tab 284 is configured to permit the thumbwheel 240 to translate distally off an end of the body 210 for removal (FIG. 30 and described further herein), unhindered by any collision between fixed tab 284 and a proximal edge of radial track 266 or a proximal edge of cutouts 260, 262. In particular, second channel 269 may be oriented and arranged to extend in a direction parallel to first channel 268, and spaced about 90° apart from first channel 268 around the circumference of thumbwheel 240.

Figure 13:
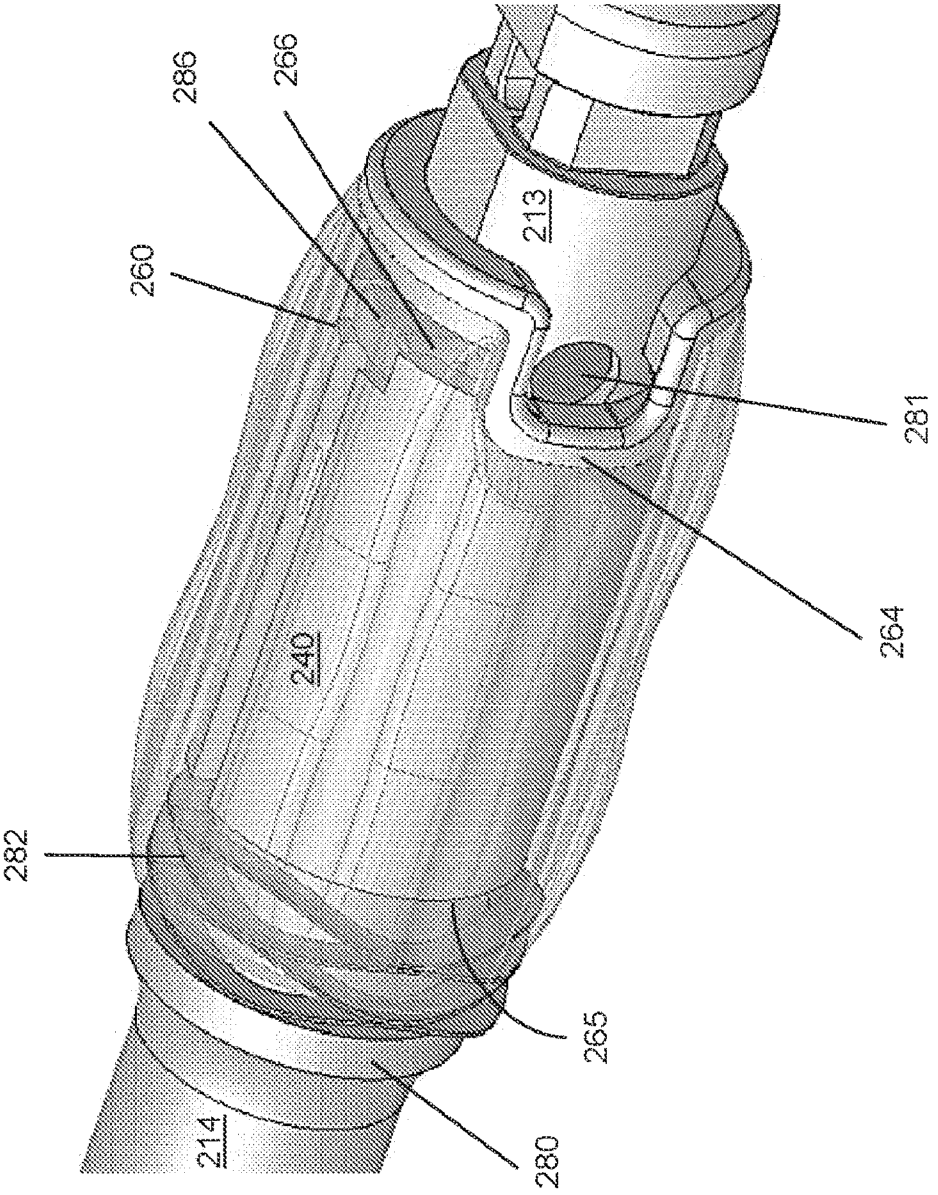
FIGS. 13-22 show perspective views of portions of an inserter according to an embodiment of FIG. 6, and further illustrate steps in methods of locking and unlocking the inserter as described herein.

With reference to FIG. 13, body 210 (e.g., proximal body member 214) may further include a flange or backing plate 280, and a biasing element 282 affixed thereto. Biasing element 282 may disposed on a distal side of backing plate 280, and may be, for example, welded or otherwise affixed thereto, such that biasing element 282 is able to engage with thumbwheel 240. Biasing element 282 may be configured to interact with a proximal abutment on an inner bore 267 of thumbwheel 240, which may be, for example, a proximal end surface 265 of cylindrical inner member 261. Biasing element 282 may be configured to bias the thumbwheel 240 in a distal direction. In certain embodiments, biasing element 282 may include a wave spring. Biasing element 282 may provide a resisting force, against which thumbwheel 240 may be translated proximally in order to actuate rotation, and which otherwise contributes to the maintenance of the position of the inserter 200 until and unless the user specifically elects to actuate the thumbwheel in the proximal direction.

Figure 23A:
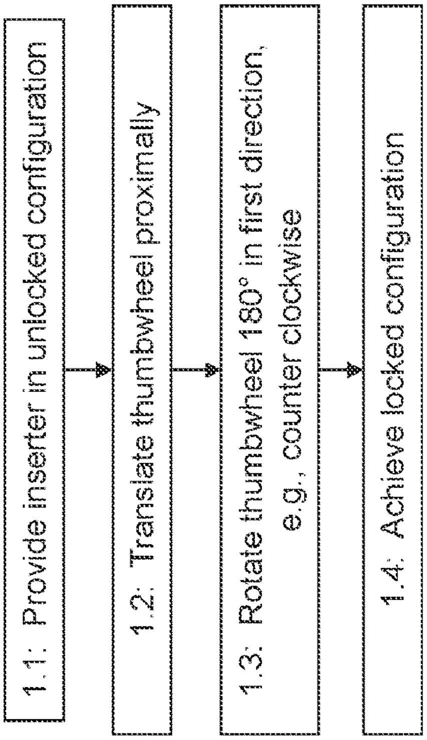
FIGS. 23A-23B illustrate flow charts providing steps in methods of locking and unlocking the inserter according to the embodiment of FIG. 6.
Figure 23B:
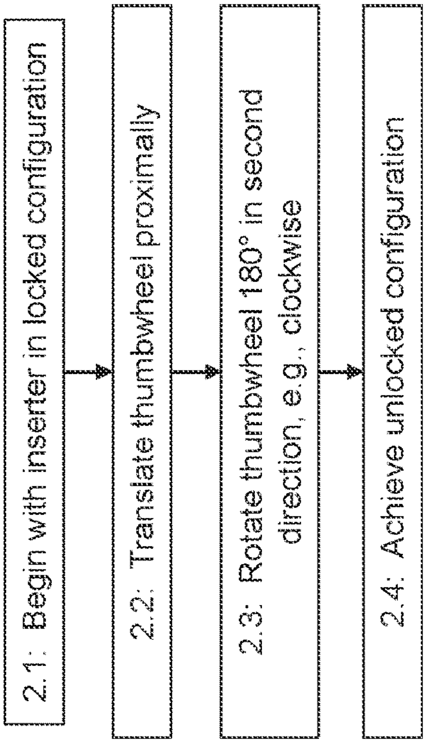

Also disclosed herein is a method for using inserter 200 during a surgical procedure, which includes a method of coupling an implant to the inserter (see FIG. 23A), and a method of decoupling the implant from the inserter after it has been placed into a patient (see FIG. 23B).

Figure 14:
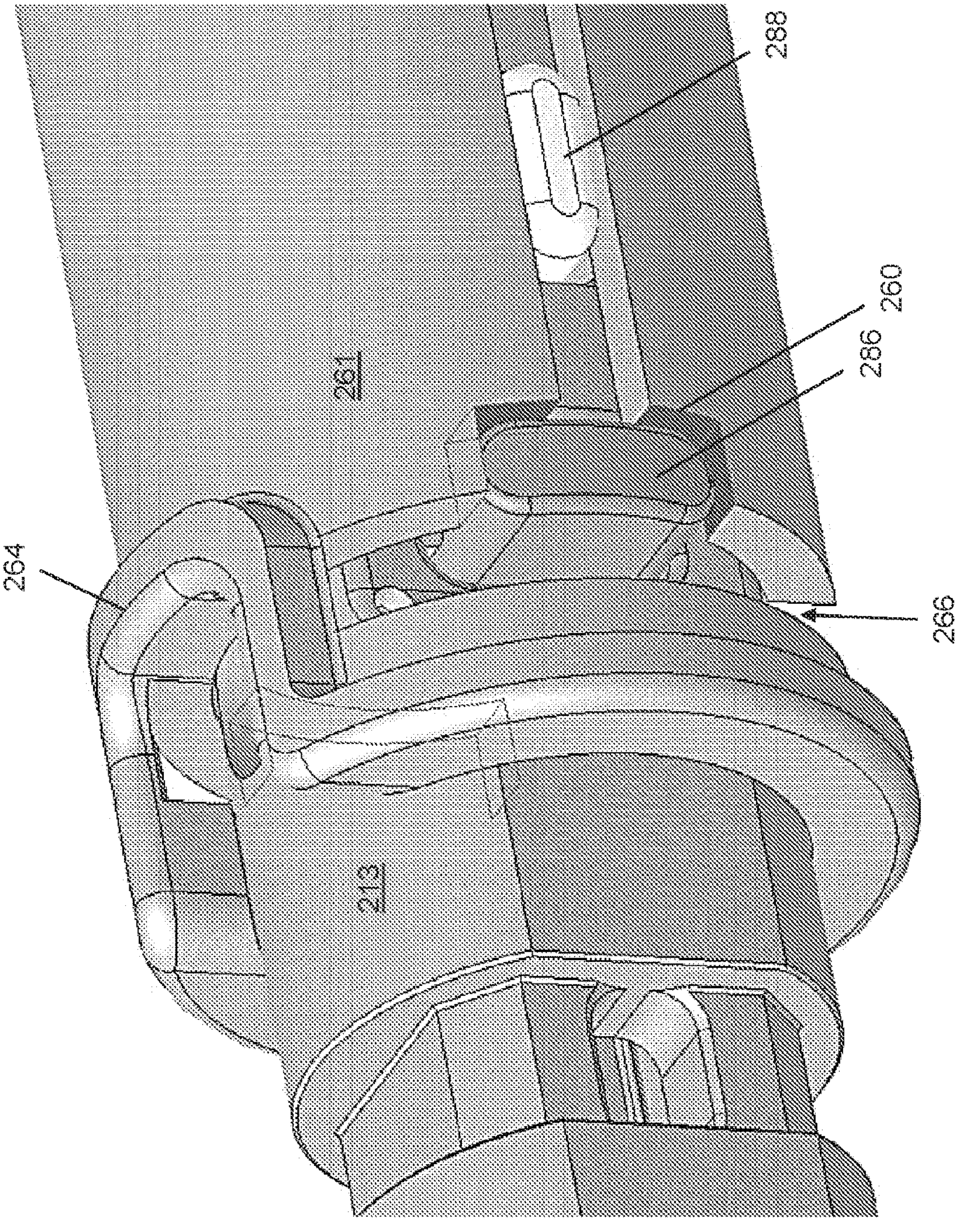
Figure 15:
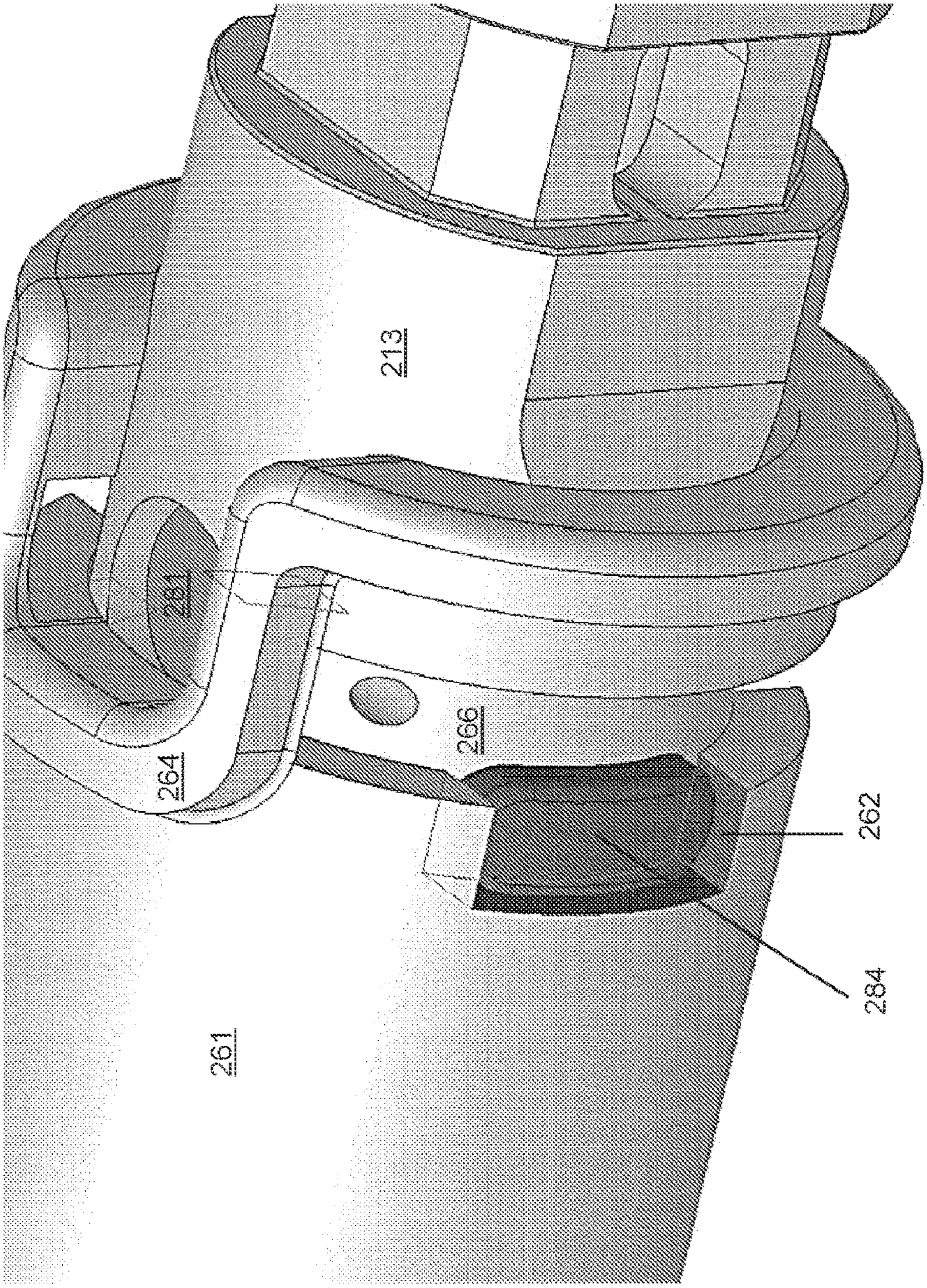
Figure 21:
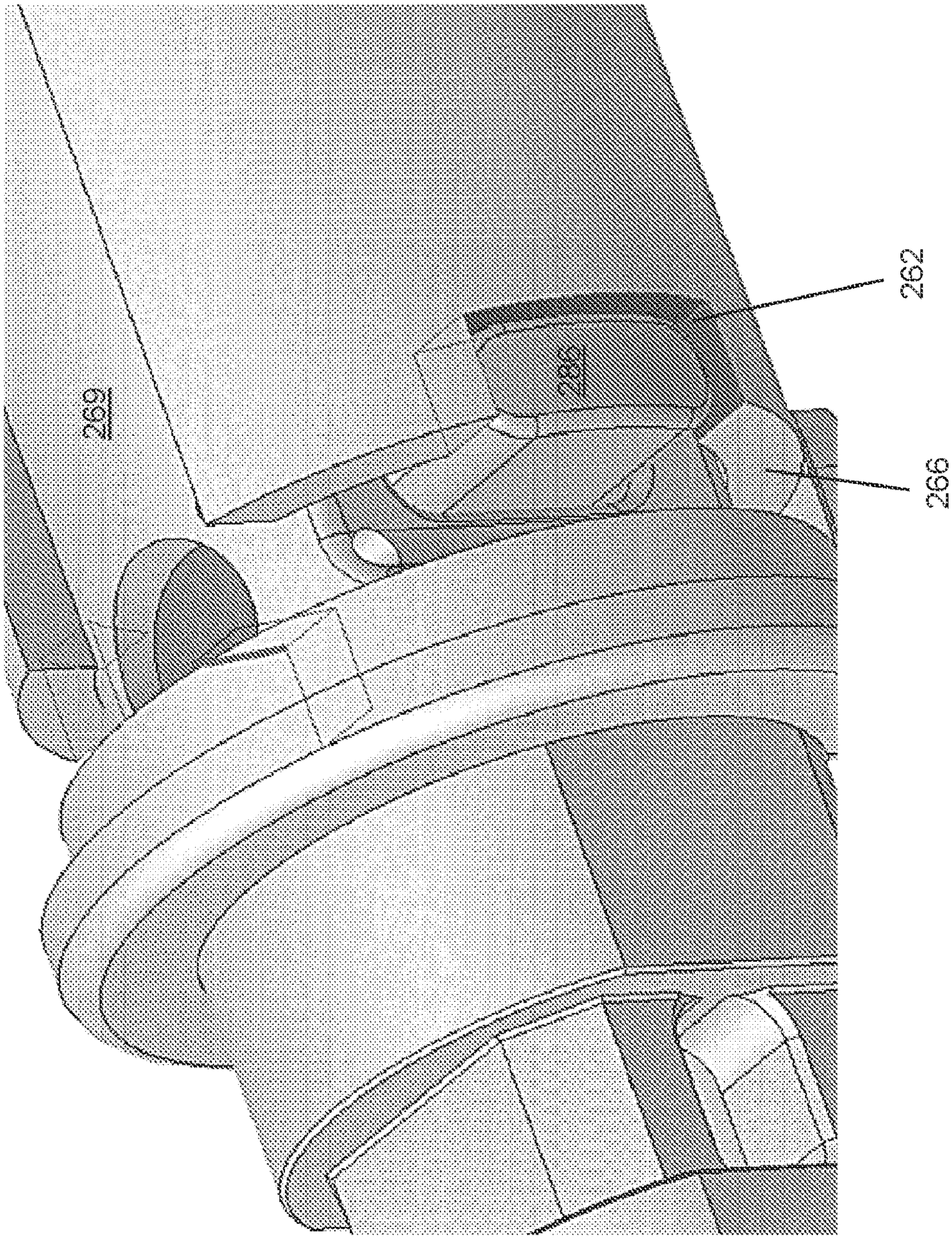
Figure 22:
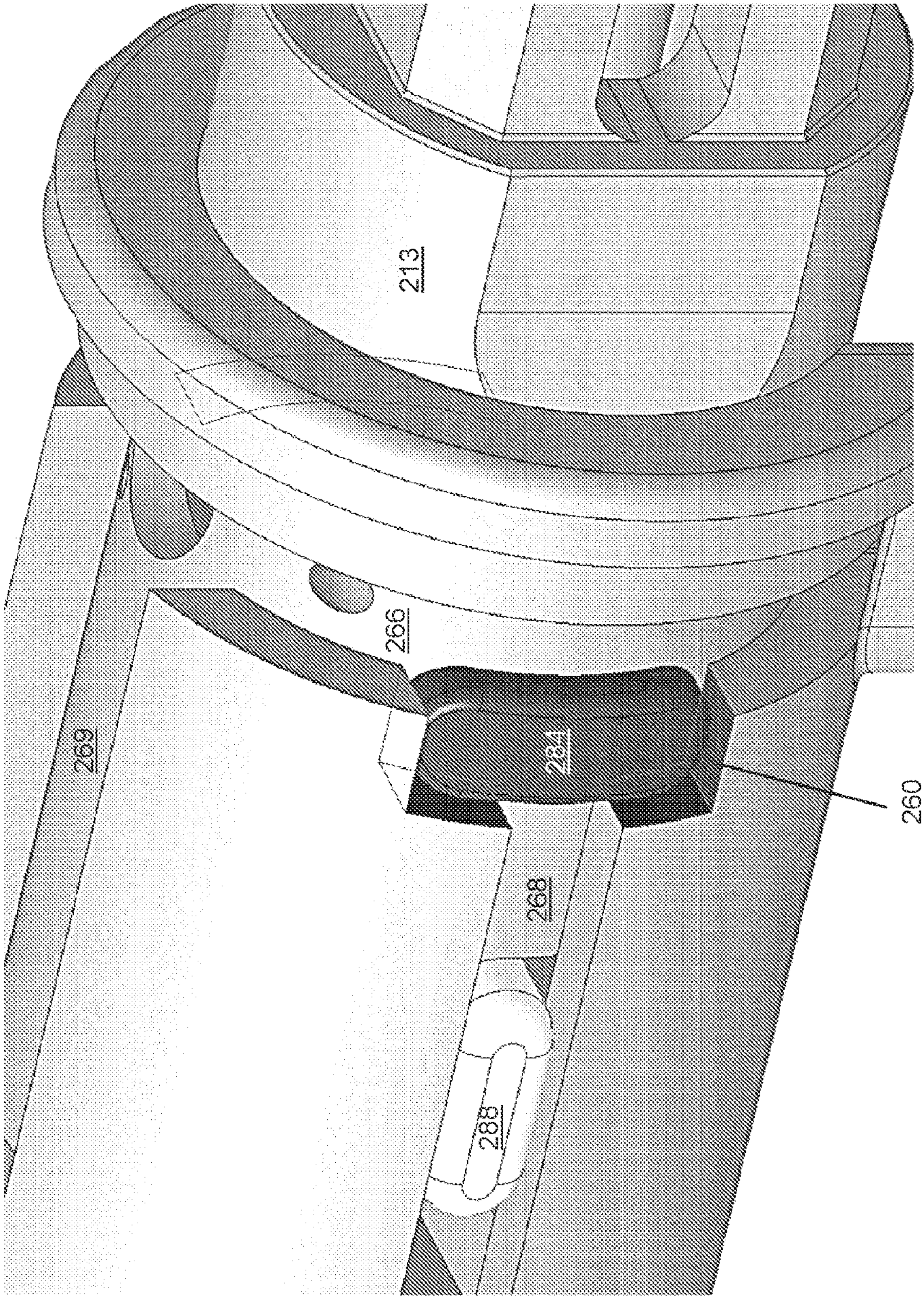

With reference to FIGS. 13-22, and the flow chart of FIG. 23A, a method of coupling an implant 10 to the inserter 200 is provided. In step 1.1, inserter 200 may be provided in an unlocked configuration, in which distal end 222 of inner shaft 220 is ready to receive and to couple to an implant 10 (see FIG. 8). With reference to FIG. 13, inserter 200 may include a visual indicator 281 on body 210, e.g., on middle body member 213, that is visible in relief 264 when inserter 200 is in the unlocked position. Visual indicator 281 may be, for example, a green button or dot, or other marking readily understandable to a user to correspond to the unlocked position. As shown in FIGS. 14-15, in the unlocked position, lock button 286 and fixed tab 284 may be disposed within or recessed into first and second cutouts 260, 262, respectively. Rotation of thumbwheel 240 is prevented by the rotational constraint on lock button 286 and fixed tab 284 by cutouts 260, 262.

Figure 16:
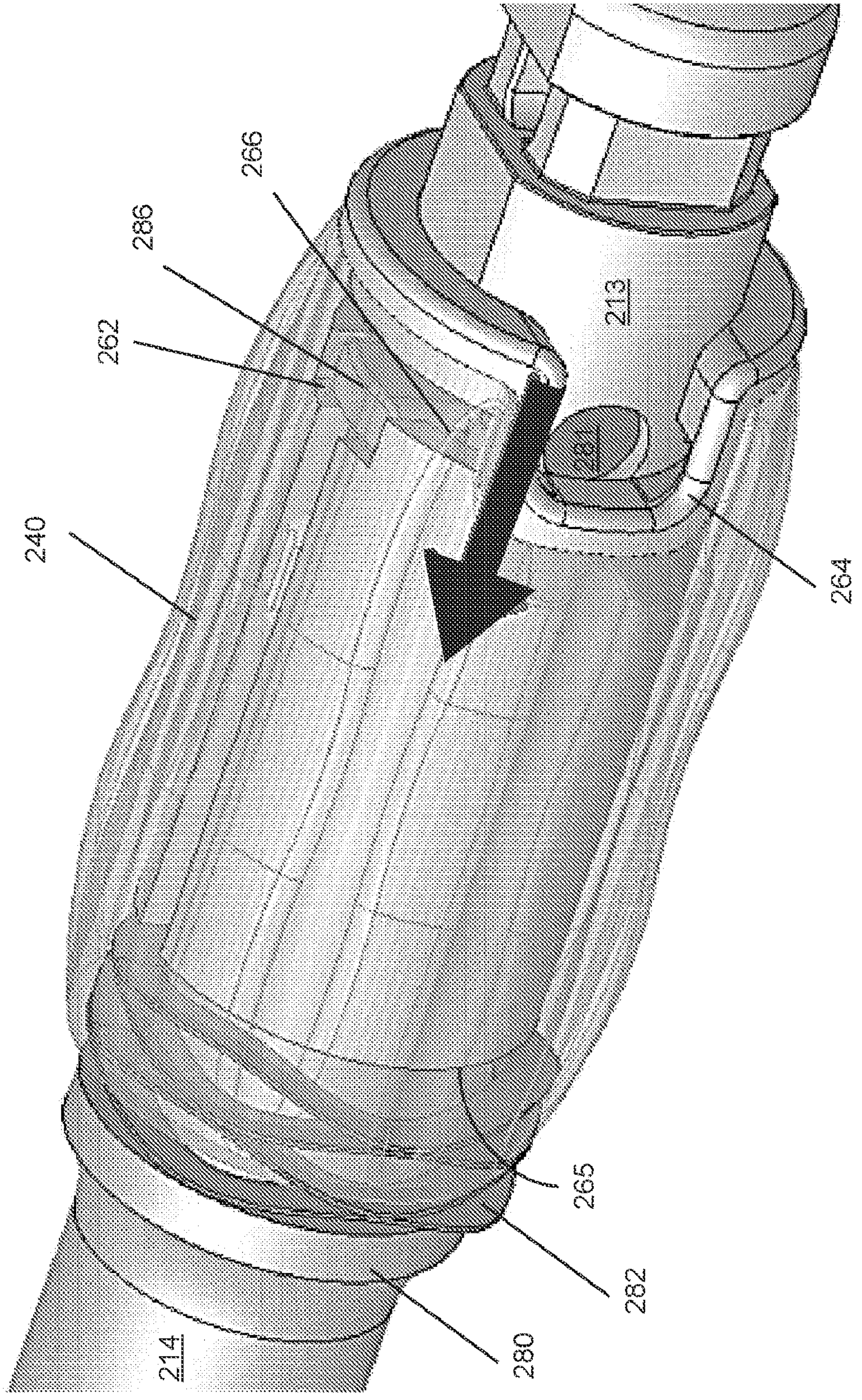
Figure 17:
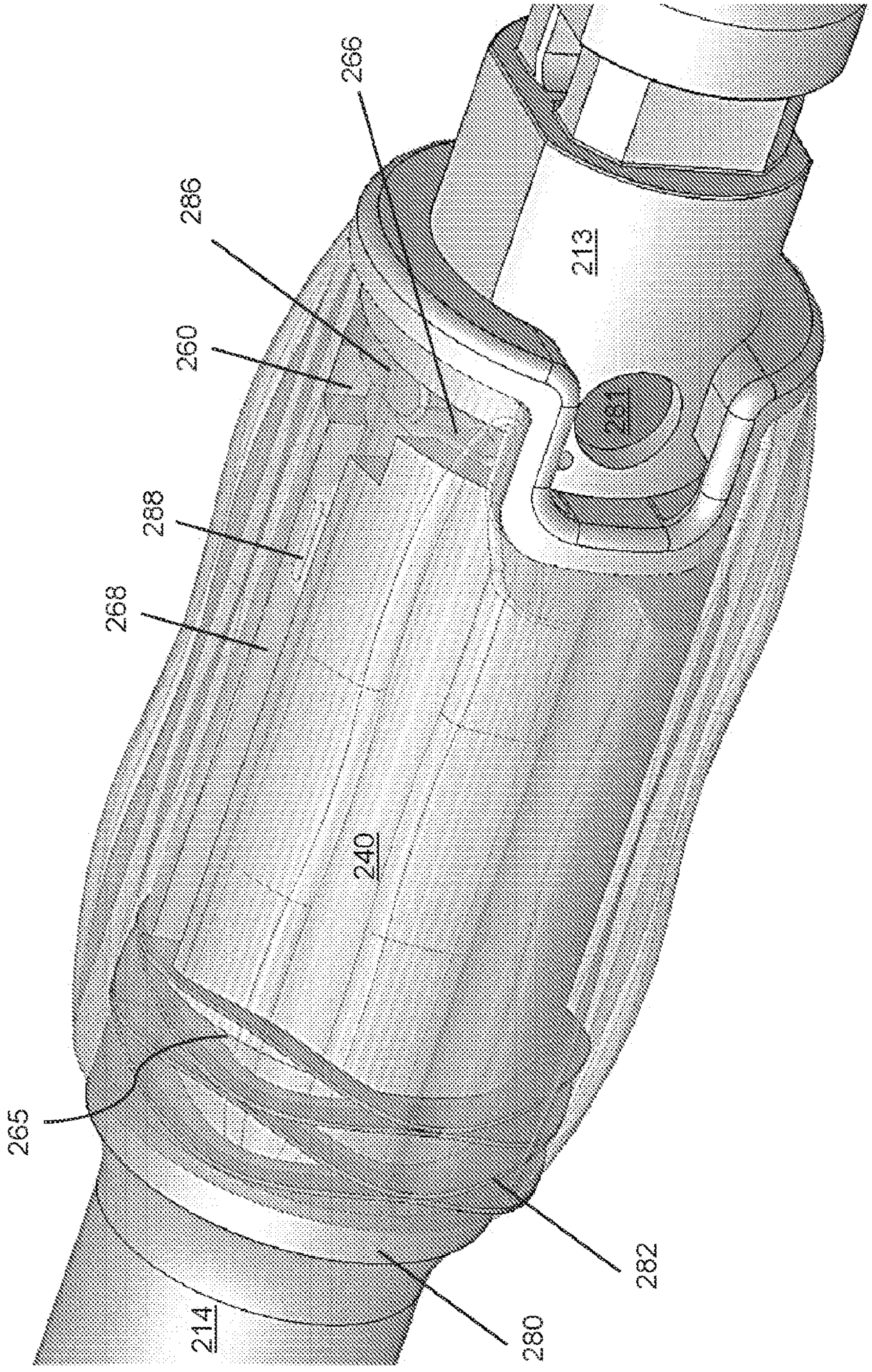
Figure 18:
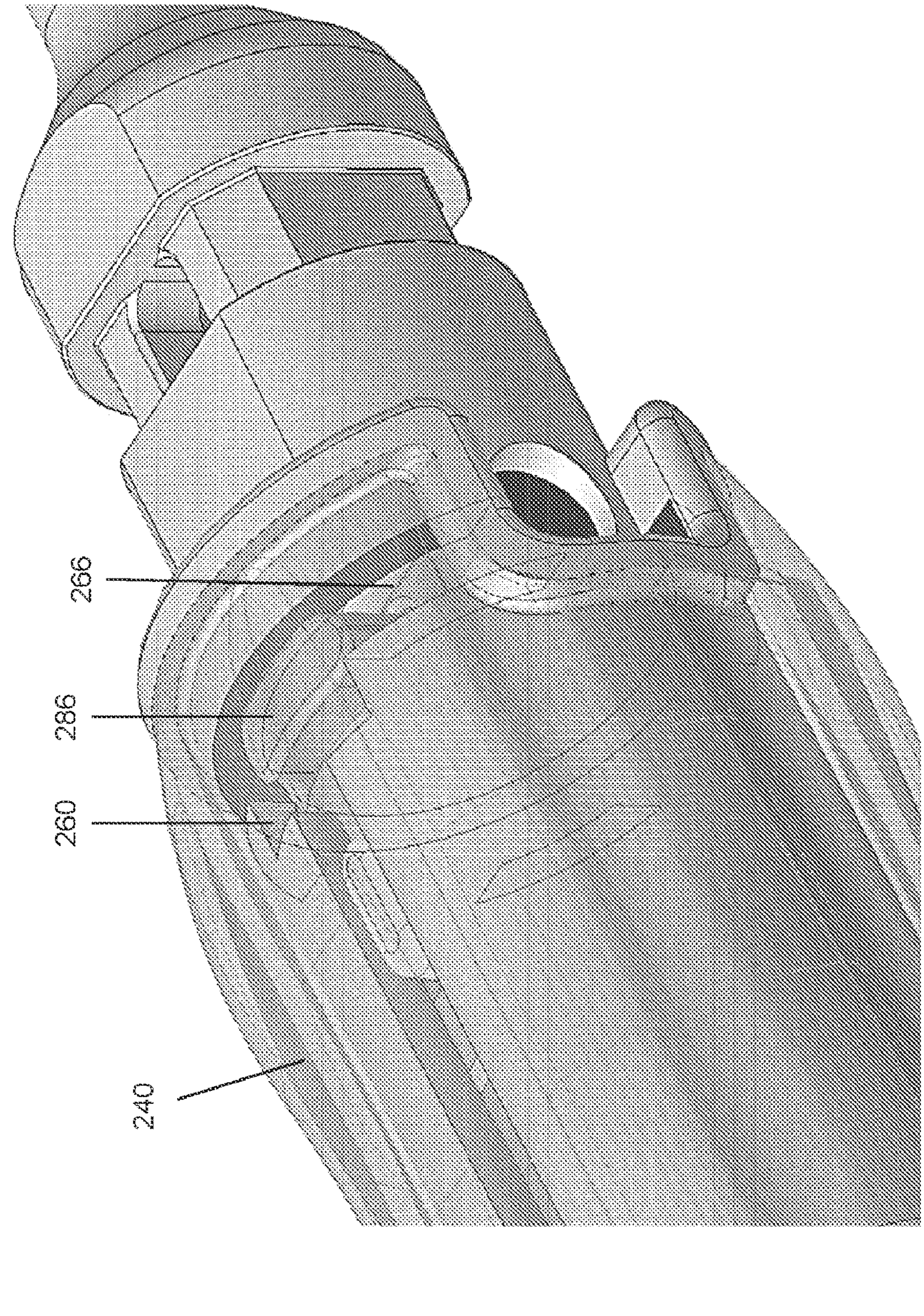
Figure 19:
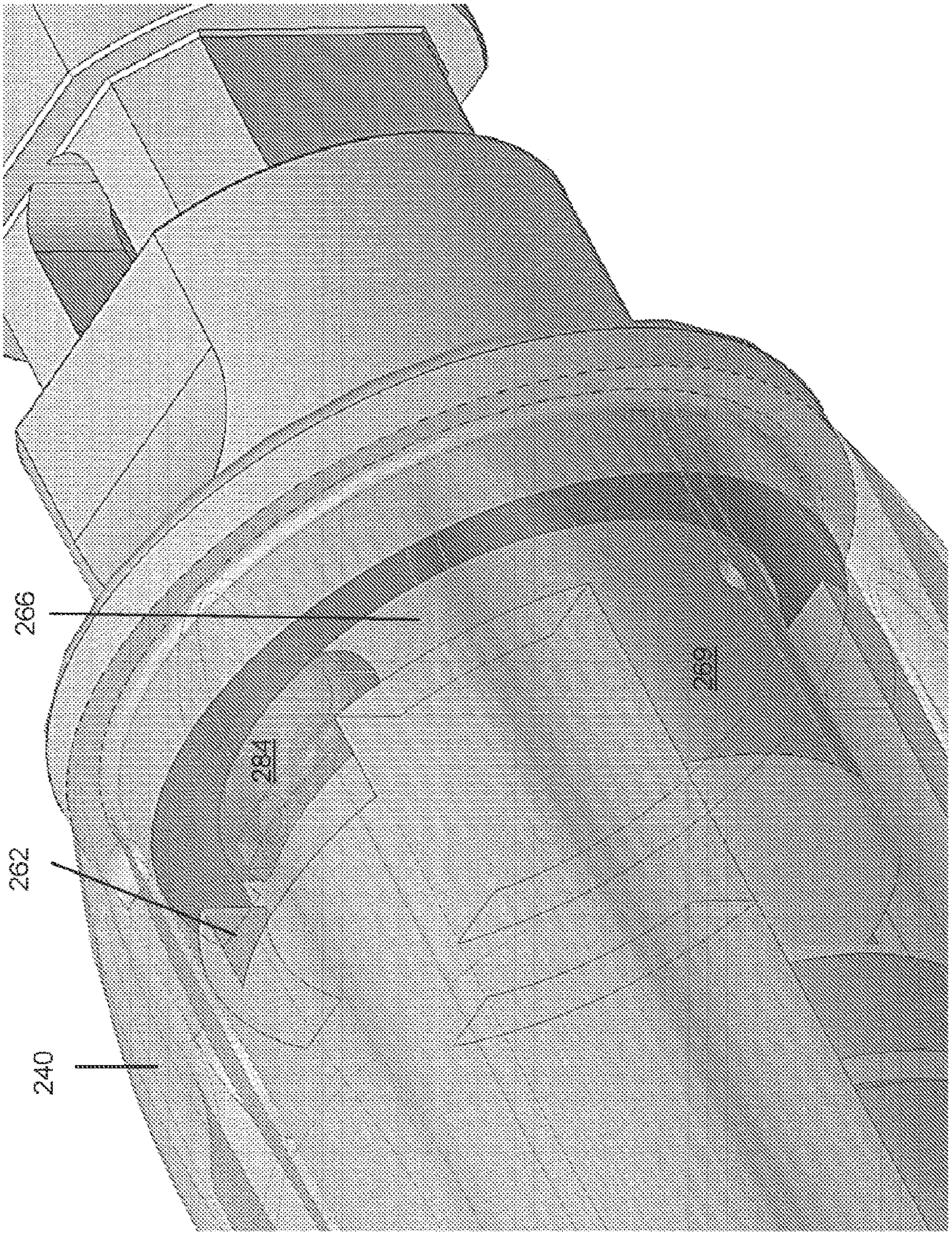
Figure 20:
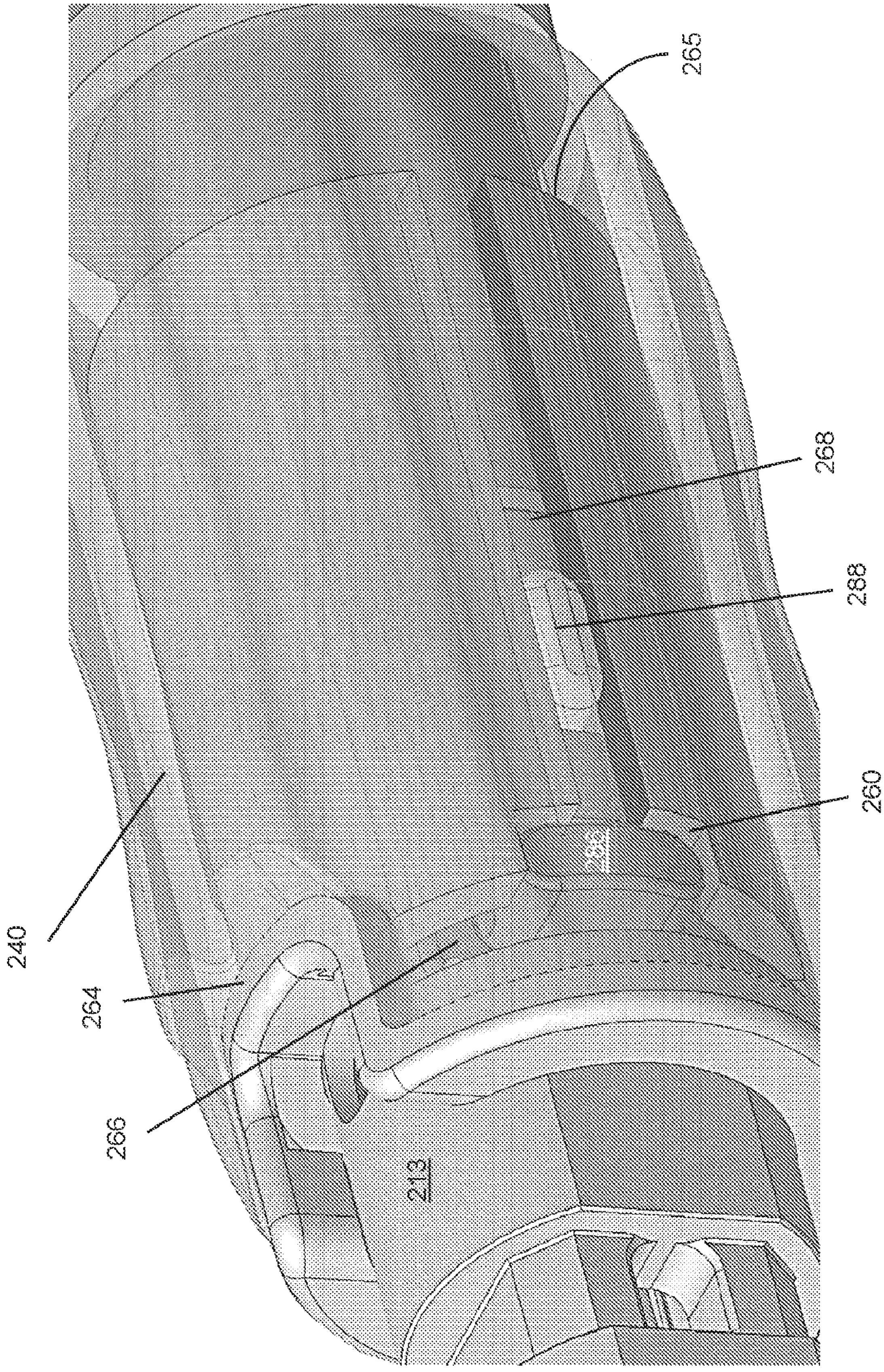

In order to release thumbwheel 240 from the unlocked position, in step 1.2, the thumbwheel 240 translates proximally against the force of biasing member 282, as shown in FIGS. 16-17. In particular, a proximal end 265 of cylindrical inner member 261 of thumbwheel 240 may contact biasing member 282. This proximal translation of thumbwheel 240 is configured to bring lock button 286 and fixed tab 284 out of cutouts 260, 262 and into axial alignment with the radial track 266, shown in FIGS. 18-19. When translated thusly, thumbwheel 240 is free to rotate relative to body 210.

In step 1.3, thumbwheel 240 may then be rotated in a first direction, e.g., clockwise or counterclockwise. In the embodiment illustrated herein, the first direction may be counterclockwise, although the orientations of features could be configured such that the first direction is instead clockwise, with the same functionality. Radial track 266 provides sufficient axial clearance for lock button 286 and fixed tab 284, thus allowing thumbwheel 240 to rotate without further translation in either a proximal or distal direction. Rotation of thumbwheel 240 may be configured to directly correspond to rotation of inner shaft 220 due to the linkage between thumbwheel 240 and inner shaft 220 provided by rotating tab 288 as described above, and shown in FIG. 20. In certain embodiments, rotating thumbwheel 240 by 180° in a counterclockwise direction from the unlocked position (see FIG. 13) moves inserter 200 from the unlocked position to the locked position, while rotating thumbwheel 240 by 90° in the counterclockwise direction from the unlocked position exposes the lock button 286 for disassembly as described further herein.

As shown in FIGS. 21-22, following rotation by 180° in the counterclockwise direction from the unlocked position, as described above, in step 1.4, the inserter 200 is configured in the locked position, in which implant 10 (see FIG. 8) is coupled to the distal tip of the inserter 200. In the locked position, the lock button 286 and fixed tab 284 are disposed within the second and first cutouts 262, 260, respectively, i.e., lock button 286 and fixed tab 284 are disposed within the opposite cutout 260, 262 from which the respective feature was located when inserter 200 was in the unlocked position. This is due to the 180° rotation of thumbwheel 240. Thumbwheel 240 is allowed to translate distally, biased by biasing member 282, precluding further rotation once second and first cutouts 262, 260 constrain lock button 286 and fixed tab 284 respectively.

With further reference to FIGS. 13-22, and the flow chart of FIG. 23B, a method is further provided for decoupling the implant 10 from the inserter after it has been placed into a patient. The steps of such method are substantially the reverse of the steps described above. In step 2.1, the process begins with the inserter in the locked configuration. This may occur, for example, immediately following positioning of the implant 10 within the intervertebral space of a patient. In step 2.2, the thumbwheel translates proximally, in order to permit rotation of the thumbwheel. In step 2.3, the thumbwheel 240 may then be rotated 180° in the direction opposite the direction of rotation in step 1.3. For example, thumbwheel 240 may rotate clockwise to return to the unlocked position, where the rotation required to achieve the locked configuration was counterclockwise. The opposite arrangement is also explicitly possible. In step 2.4, the unlocked configuration is achieved, and the thumbwheel is allowed to translate distally, biased by biasing member 282, precluding further rotation.

Figure 30:
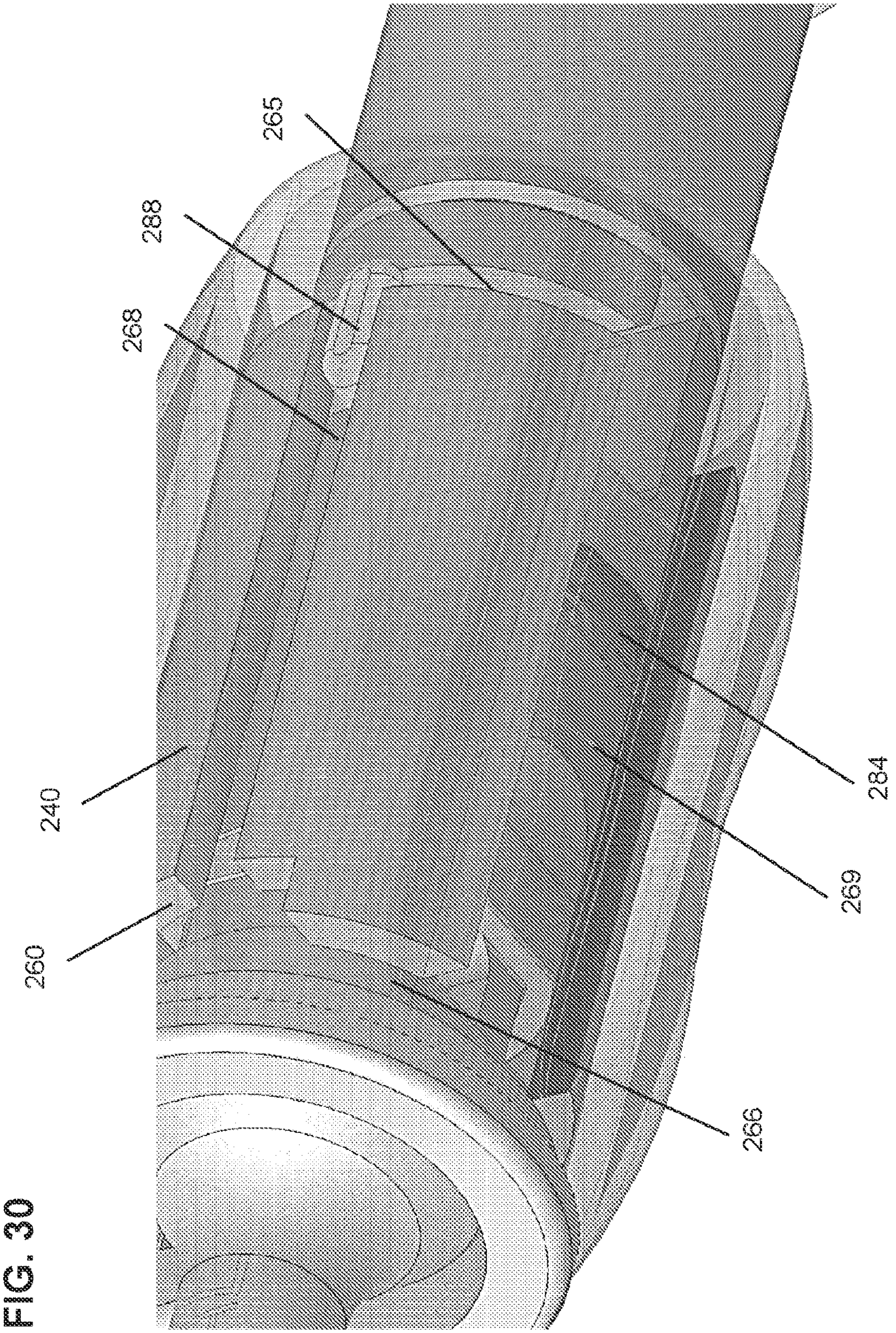
Figure 31B:
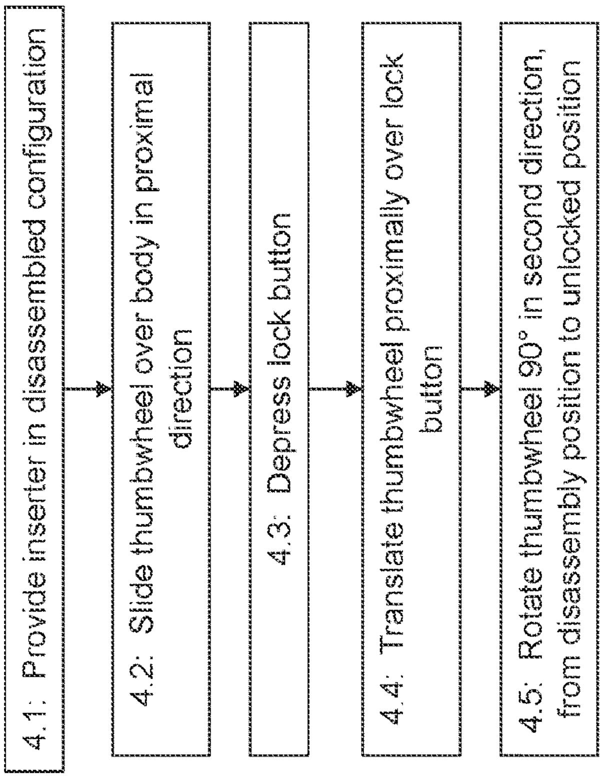
FIGS. 31A-31B illustrate flow charts providing steps in methods of disassembling and assembling the inserter according to the embodiment of FIG. 6.
Figure 31A:
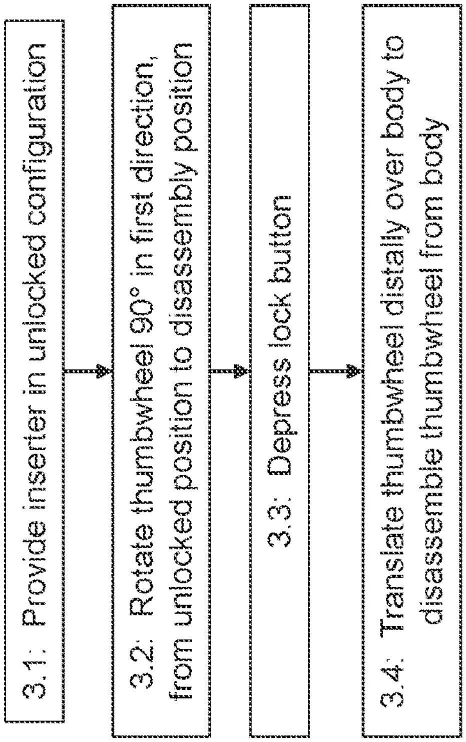

With reference to FIGS. 24-30, and the flow chart of FIG. 31A, also disclosed herein is a method for dismantling or disassembling inserter 200, which may be useful, e.g., following use during a surgical procedure, or for cleaning or sterilization of the instrument.

Figure 24:
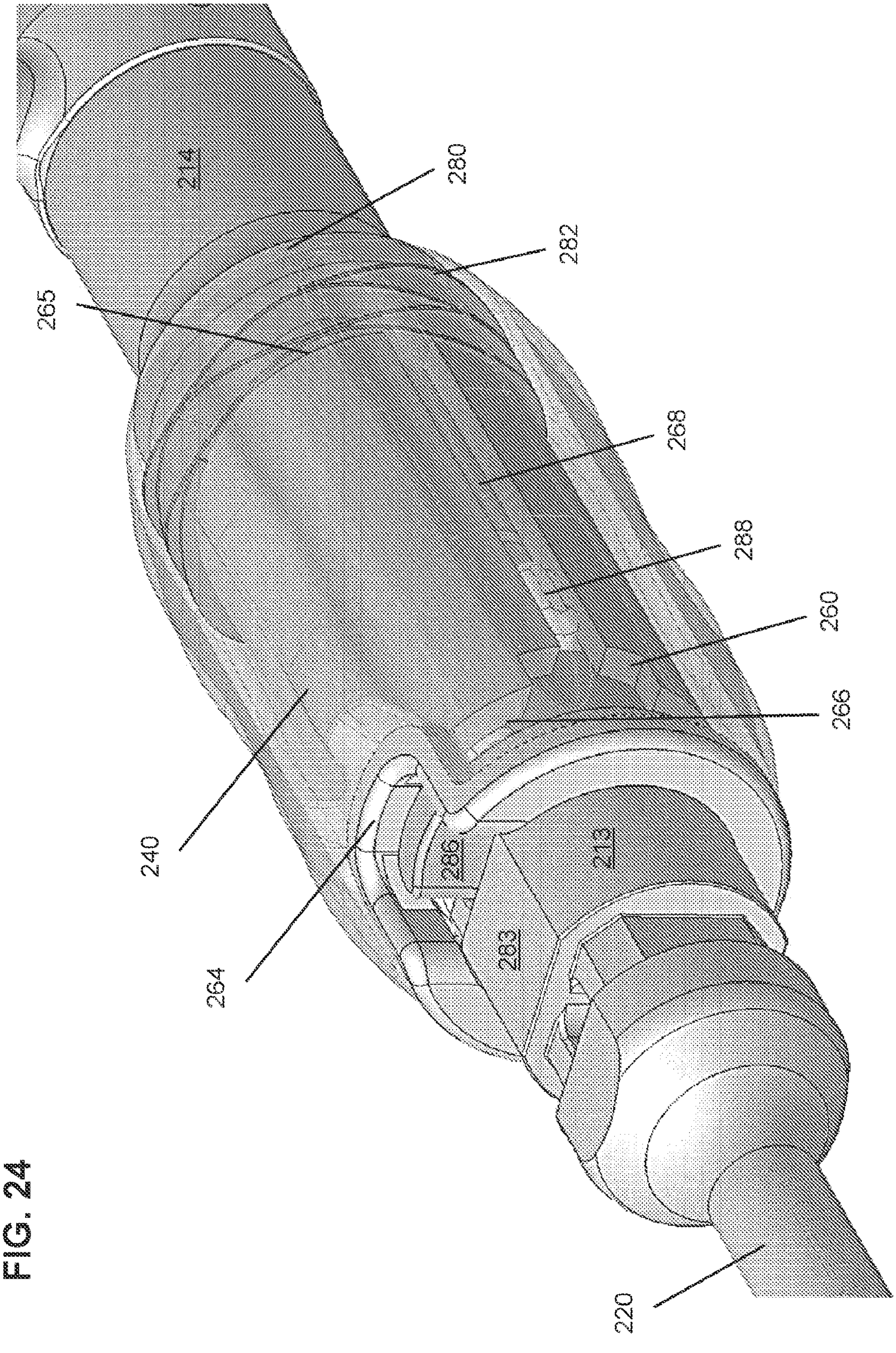
FIGS. 24-30 show perspective views of portions of an inserter according to an embodiment of FIG. 6, and further illustrate steps in method of disassembling the inserter as described herein.
Figure 25:
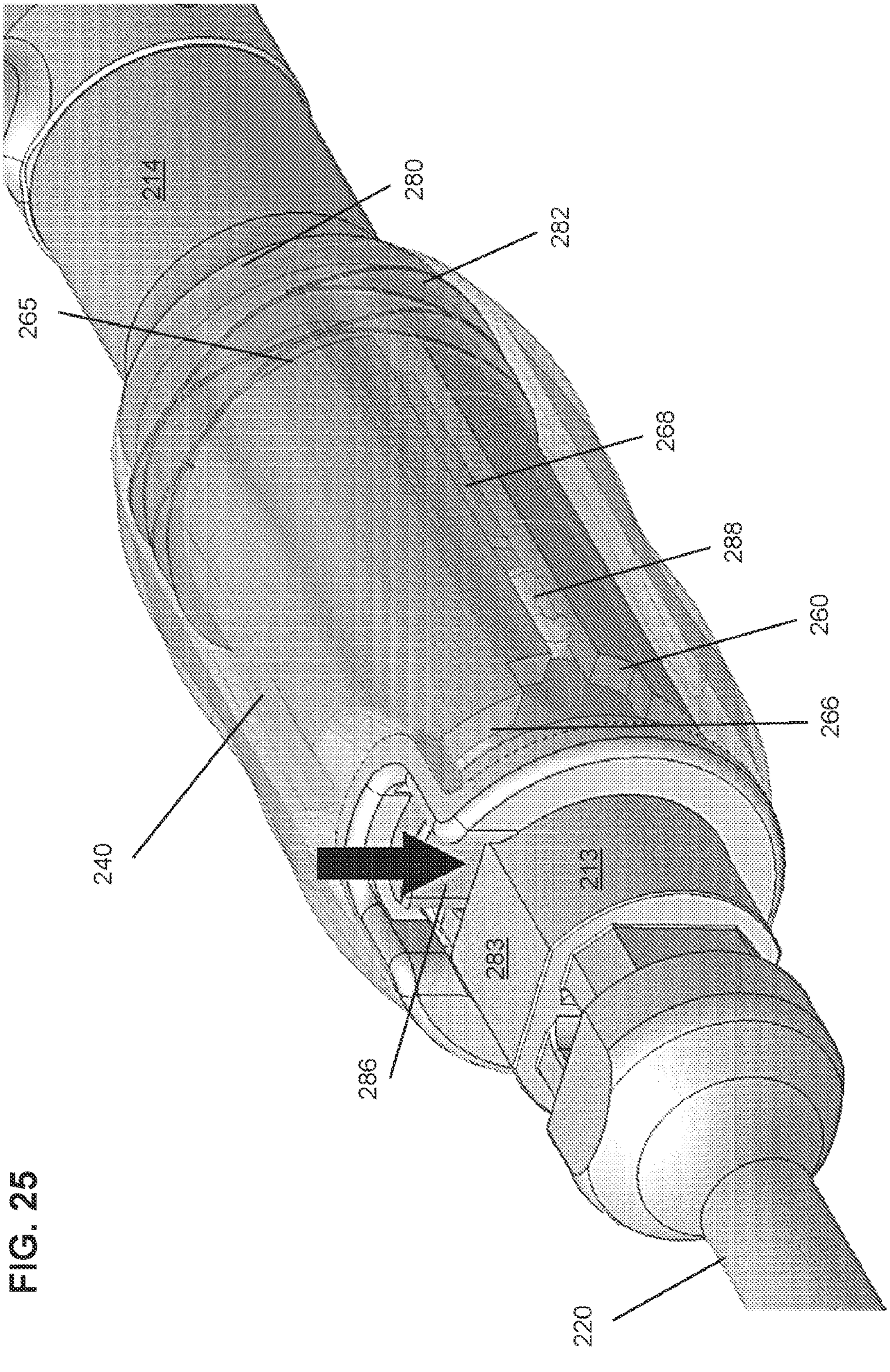
Figure 26:
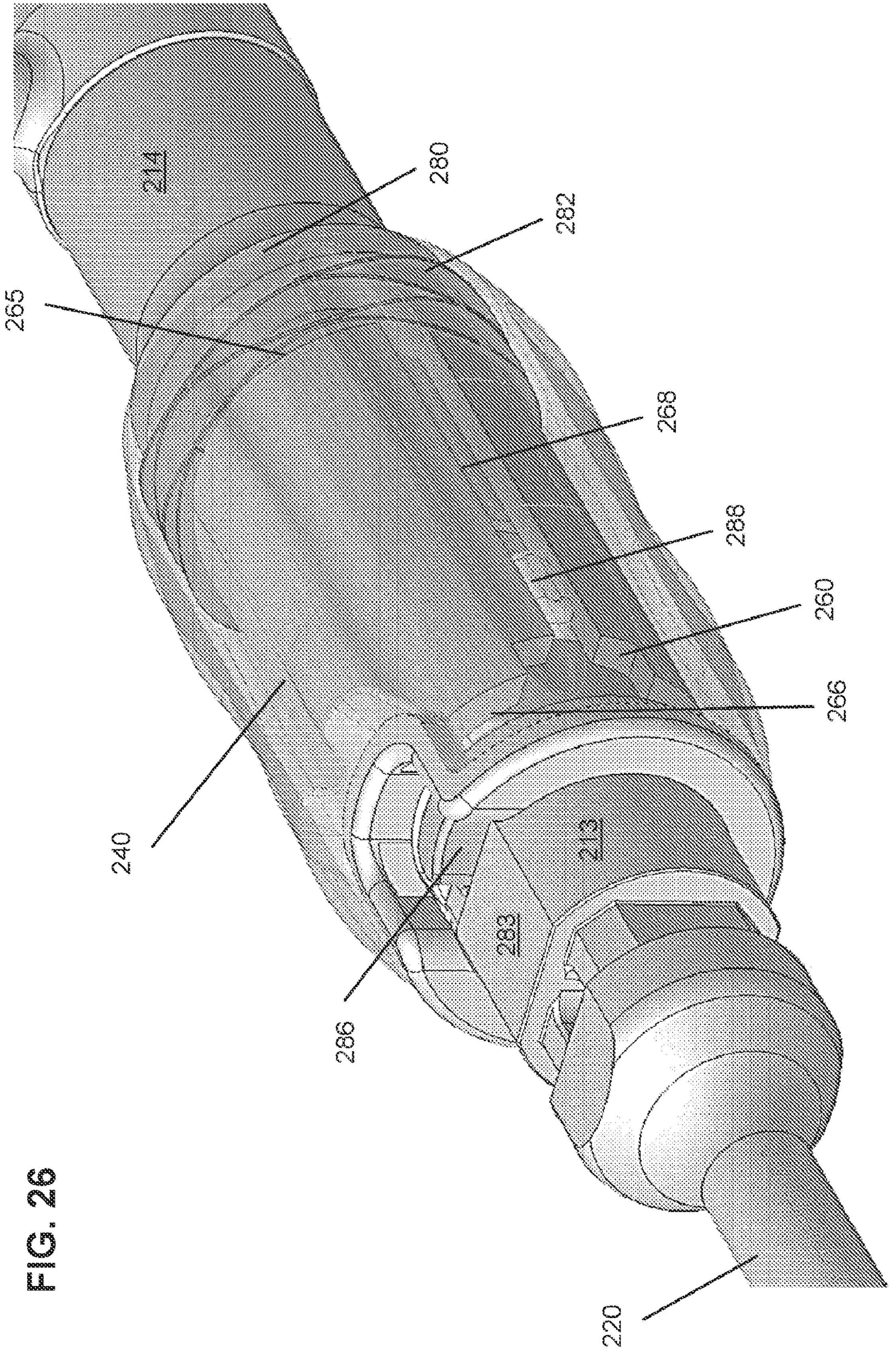
Figure 27:
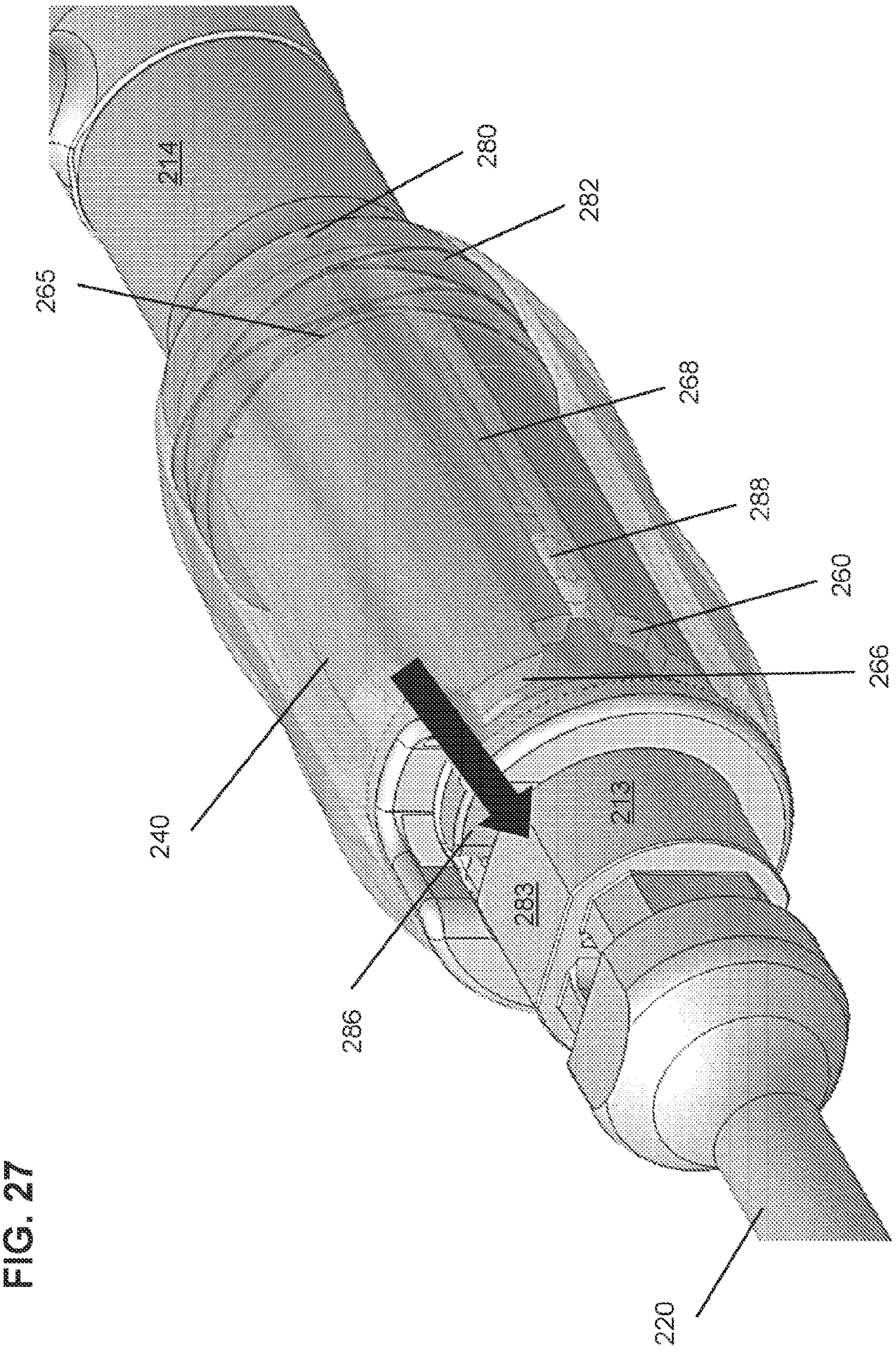
Figure 28:
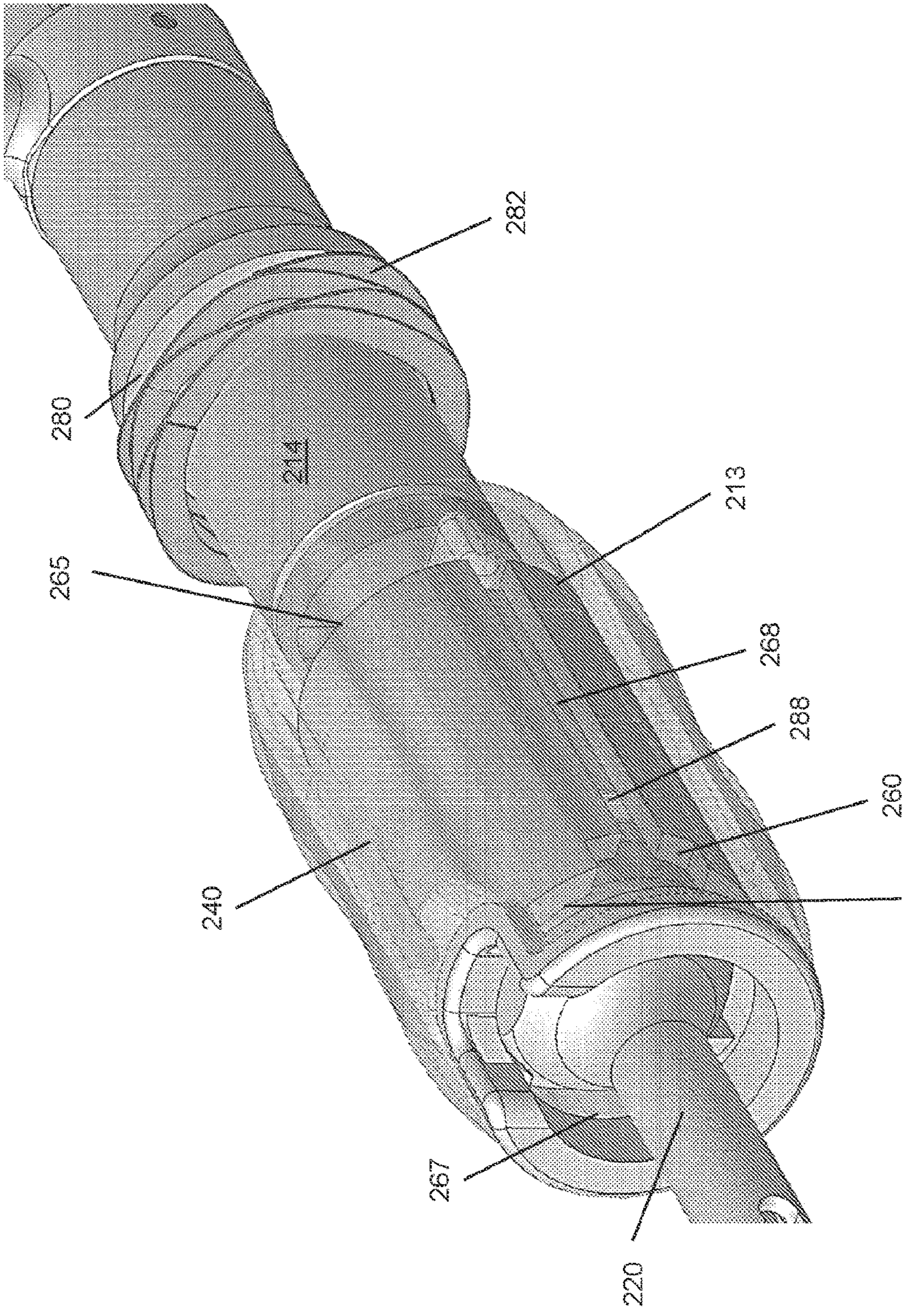
Figure 29:
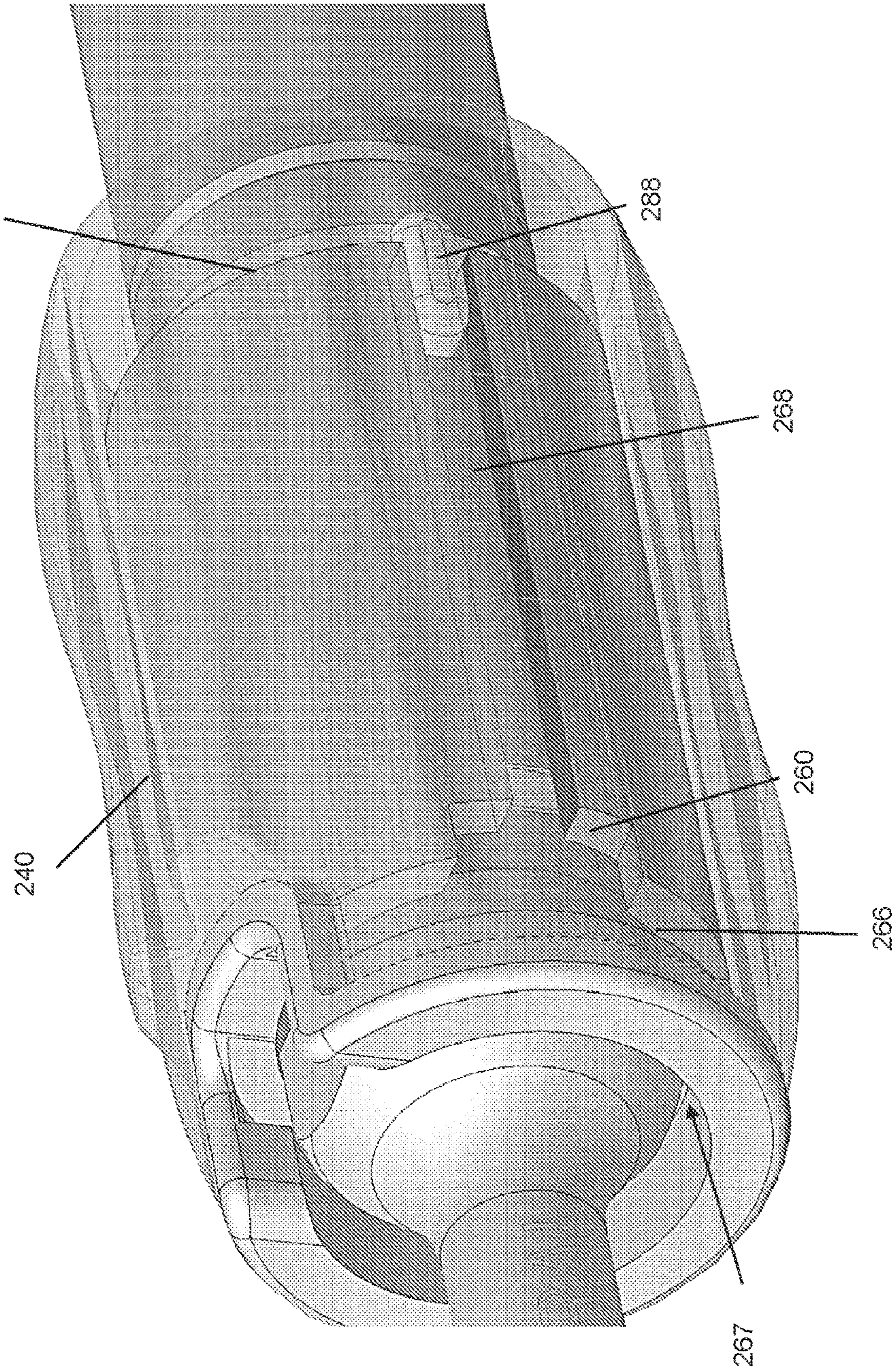

In disassembly step 3.1, the inserter 200 is provided in the unlocked configuration. In step 3.2, thumbwheel 240 is rotated 90° from its unlocked position, such that lock button 286 is entirely visible within relief 264, as shown in FIG. 24. In step 3.3, lock button 286 is depressed fully (FIG. 25), so that it sits below the inner bore 267 of thumbwheel 240. Lock button 286 is thus substantially flush with the surface of body 210, e.g., middle body member 213 (FIG. 26). With lock button 286 no longer constraining thumbwheel 240, the thumbwheel 240 is released and, in step 3.4, translates distally (FIG. 27). As shown in FIG. 28, biasing member 282 may be affixed to backing plate 280 on proximal body member 214, and therefore may not translate with thumbwheel 240. In step 3.4, thumbwheel 240 translates distally off of body 210 of inserter 200. As this occurs, channels 268 and 269 will permit rotating tab 288 and fixed tab 284, respectively, to remain in place (FIG. 29) even as the thumbwheel 240 translates distally (FIG. 30).

With reference to FIGS. 24-30, and the flow chart of FIG. 31B, also disclosed herein is a method for assembling inserter 200, which may be useful, e.g., prior to use during a surgical procedure, or after cleaning or sterilization of the instrument. The steps of such method are substantially the reverse of the steps described above relative to FIG. 31A, and may be performed before, after, or independently thereof.

In assembly step 4.1, the inserter is provided in the disassembled configuration, e.g., prior to use or following sterilization or cleaning procedures. In assembly step 4.2, the thumbwheel 240 slides over the body from the distal end, e.g., over the outer shaft 212 in a proximal direction. When the proximal end of thumbwheel 240 reaches the lock button 286, in step 4.3, the lock button 286 is depressed in order to allow thumbwheel 240 to slide over the lock button 286. In step 4.4, the thumbwheel 240 translates proximally over the lock button 286, e.g., until it abuts biasing member 282. In step 4.5, the thumbwheel 240 may then be rotated 90° in the second direction from its disassembly position (FIG. 24) to the unlocked position. Inserter 200 is then ready for use, e.g., to couple to an implant as described above relative to the drawings and the flow chart of FIG. 23A.

In addition to the inserter 200 and the methods described above, it is also considered that in another embodiment, a system is provided for use in a spinal fusion procedure, including the inserter 200 substantially as described above, together with a spinal fusion implant 10 (see FIG. 8). Suitable spinal fusion implants are known in the art.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An inserter for inserting a spinal fusion implant, the inserter comprising:

a housing having a proximal member and a housing shaft extending distally therefrom;

an inner shaft having a distal end and a proximal end, wherein the inner shaft is configured to be disposed at least partially within the housing shaft and translate relative to the housing shaft and the distal end is configured to releasably engage a spinal fusion implant;

a thumbwheel positioned partially within the proximal member of the housing and rotatably fixed to the proximal end of the inner shaft, wherein the thumbwheel is configured to rotate about a longitudinal axis of the inserter and cause the inner shaft to rotate;

a lock positioned at a proximal end of the housing, wherein the lock is configured to receive the proximal end of the inner shaft and configured to move between a locked position and an unlocked position, wherein in the locked position, the inner shaft is rotatably fixed to the thumbwheel, and in the unlocked position, the inner shaft and the thumbwheel are separable from one another; and a soft stop configured to provide one or more of audible and or tactile feedback to a user to indicate that the spinal fusion implant is fully disengaged from the distal end of the inner shaft, wherein the soft stop comprises a body, a slider body comprising a threaded aperture configured to threadedly engage threads on the body, a biasing member proximal to the slider body, and a biasing member distal to the slider body.

2. The inserter of claim 1, wherein the distal end of the inner shaft comprises threads configured to engage complementary threads on the spinal fusion implant.

3. The inserter of claim 1, wherein rotation of the thumbwheel in a first direction is configured to cause the distal end of the inner shaft to engage the spinal fusion implant, and rotation of the thumbwheel in a second direction is configured to cause the distal end of the inner shaft to disengage from the spinal fusion implant.

4. The inserter of claim 1, wherein, in the unlocked position:

the inner shaft is configured to translate distally, causing the proximal end thereof to disengage from the thumbwheel, and the inner shaft is further configured to be removed from a distal end of the housing shaft.

5. The inserter of claim 4, wherein the thumbwheel further comprises a biasing element configured to bias the thumbwheel in a distal direction, wherein in the unlocked position, the thumbwheel is configured to translate proximally against a force of the biasing element, and when the proximal end of the inner shaft is disengaged from the thumbwheel, a distal end of the thumbwheel is configured to move radially outward relative to the longitudinal axis to initiate disassembly of the thumbwheel from the inserter.

6. The inserter of claim 1, wherein the proximal end of the inner shaft comprises a keyed feature which provides a complementary fit with a corresponding keyed feature on the thumbwheel.

7. The inserter of claim 6, wherein the keyed feature is a male hex feature, and the corresponding keyed feature is a female hex feature.

8. The inserter of claim 1, wherein the inner shaft has a first diameter, and wherein the lock further comprises:

a portion of the inner shaft having a second diameter that is reduced relative to the first diameter; and a lock button disposed on the housing and movable in a direction substantially perpendicular to the longitudinal axis, the lock button comprising a slot configured to engage the portion of the inner shaft having the reduced diameter, wherein the slot has an irregular cross sectional shape, such that:

in the locked position, an outer surface of the lock button is substantially flush with an outer surface of the housing, and a first end of the slot provides a close fit with the portion of the inner shaft having the reduced diameter, and in the unlocked position, the outer surface of the lock button is raised relative to the outer surface of the housing, and a second end of the slot accommodates the inner shaft at a portion not having the reduced diameter, allowing the inner shaft to translate.

9. The inserter of claim 8, wherein the lock further comprises:

a track extending within the lock button in a direction parallel to the direction in which the lock button is movable;

a pin disposed within the track;

a plunger disposed within the housing and configured to engage the lock button in the locked position and the unlocked position;

a spring configured to engage the plunger; and a screw configured to maintain a position of the plunger and the spring.

10. The inserter of claim 9, wherein the housing further comprises a first through-hole configured to engage the plunger in the unlocked position, and a second through-hole configured to engage the plunger in the locked position.

11. The inserter of claim 1, wherein the soft stop comprises:

a keyed distal end feature configured to rotatably engage a complementarily keyed feature on a proximal end of the thumbwheel, wherein the keyed distal end feature is coupled to a longitudinally extending body having a plurality of threads disposed thereon;

a slider body configured to threadedly engage the longitudinally extending body and to translate within the soft stop; and a first wave spring and a second wave spring disposed at opposite ends of the slider body, respectively.

12. The inserter of claim 11, wherein the thumbwheel is configured to be rotatable after the slider body abuts the first wave spring or the second wave spring.

13. A system comprising:

the inserter of claim 1; and the spinal fusion implant.

* * * * *